US012678474B2

(12) United States Patent
Zhu et al.

(10) Patent No.: US 12,678,474 B2
(45) Date of Patent: Jul. 14, 2026

(54) SCREENING OF FIXED-POINT COUPLING SITES OF CYSTEINE-MODIFIED ANTIBODY-TOXIN CONJUGATE (TDC)

(71) Applicant: SICHUAN BAILI PHARMACEUTICAL CO. LTD., Chengdu (CN)

(72) Inventors: Yi Zhu, Chengdu (CN); Yiqian Wang, Chengdu (CN); Shi Zhuo, Chengdu (CN); Jie Li, Chengdu (CN); Yongguo Yu, Chengdu (CN); Weili Wan, Chengdu (CN)

(*) Notice: Subject to any disclaimer, the term of this patent is extended or adjusted under 35 U.S.C. 154(b) by 1365 days.

(21) Appl. No.: 16/976,475

(22) PCT Filed: Jun. 15, 2018

(86) PCT No.: PCT/CN2018/091623
§ 371 (c)(1),
(2) Date: Aug. 28, 2020

(87) PCT Pub. No.: WO2018/233572
PCT Pub. Date: Dec. 27, 2018

(65) Prior Publication Data
US 2021/0393794 A1 Dec. 23, 2021

(30) Foreign Application Priority Data
Jun. 20, 2017 (CN) ......................... 201710469761.5

(51) Int. Cl.
*A61K 47/68* (2017.01)
*A61K 38/07* (2006.01)

(52) U.S. Cl.
CPC ........ *A61K 38/07* (2013.01); *A61K 47/68031* (2023.08); *A61K 47/68035* (2023.08);
(Continued)

(58) Field of Classification Search
CPC combination set(s) only.
See application file for complete search history.

(56) References Cited

U.S. PATENT DOCUMENTS 9,504,756 B2 11/2016 Lyon et al.

FOREIGN PATENT DOCUMENTS

CN 103648532 A 3/2014
CN 106029083 Y 10/2016
(Continued)

OTHER PUBLICATIONS

Junutula, Jr. et al. "Site-Specific Conjugation of a Cytotoxic Drug to an Antibody Improves the Therapeutic Index" Nat Biotechnol, vol. 26, No. (8), Jul. 20, 2008 (Jul. 20, 2008), pp. 925-932.

*Primary Examiner* — Jeffrey Stucker
*Assistant Examiner* — Laura Ann Essex

(57) ABSTRACT

Disclosed in the present invention is a cysteine-modified antibody-toxin conjugate. The cysteine-modified antibody-toxin conjugate is characterized in that: the antibody is an antibody in which cysteine is inserted on a fixed point, and insertion sites of the cysteine comprising one or more of the following sites: a 110th site, a IIIth site and a 142th site of a light chain in a Kappa/λ light chain constant region, and a 254th site, a 255th site, a 258th, a 259th site, a 354th site, a 355th site, a 357th site, a 378th site, a 379th site, a 386th site, a 387th site or a 410th site of a heavy chain of a heavy chain constant region of an IgG antibody.

10 Claims, 8 Drawing Sheets
(5 of 8 Drawing Sheet(s) Filed in Color)
Specification includes a Sequence Listing.

(52) U.S. Cl.
CPC .... *A61K 47/68037* (2023.08); *A61K 47/6807* (2017.08); *A61K 47/6817* (2017.08); *A61K 47/6845* (2017.08); *A61K 47/6889* (2017.08)

(56) References Cited

FOREIGN PATENT DOCUMENTS

| | | | | | |
|---|---|---|---|---|---|
| WO | WO2014124316 | Y | | 8/2014 | |
| WO | WO2015138615 | A | | 9/2015 | |
| WO | WO2015157595 | | | 10/2015 | |
| WO | WO-2015157595 | A1 | * | 10/2015 | ............. A61K 47/68 |
| WO | WO-2016040856 | A2 | * | 3/2016 | ......... A61K 47/6803 |

* cited by examiner

SEQUENCE LISTING

```
<160> NUMBER OF SEQ ID NOS: 59

<210> SEQ ID NO 1
<211> LENGTH: 348
<212> TYPE: DNA
<213> ORGANISM: Artificial Sequence
<220> FEATURE:
<223> OTHER INFORMATION: synthesized

<400> SEQUENCE: 1

gatgtgcagc ttcaggagtc gggacctagc ctggtgaaac cttctcagtc tctgtccctc      60

acctgcactg tcactggcta ctcaatcacc agtgattttg cctggaactg gattcggcag     120

tttccaggaa acaagctgga gtggatgggc tacataagtt atagtggtaa cactaggtac     180

aacccatctc tcaaaagtcg aatctctatc actcgcgaca catccaagaa ccaattcttc     240

ctgcagttga actctgtgac tattgaggac acagccacat attactgtgt aacggcggga     300

cgcgggtttc cttattgggg ccaagggact ctggtcactg tctctgca                  348


<210> SEQ ID NO 2
<211> LENGTH: 116
<212> TYPE: PRT
<213> ORGANISM: Artificial Sequence
<220> FEATURE:
<223> OTHER INFORMATION: synthesized

<400> SEQUENCE: 2

Asp Val Gln Leu Gln Glu Ser Gly Pro Ser Leu Val Lys Pro Ser Gln
1               5                   10                  15

Ser Leu Ser Leu Thr Cys Thr Val Thr Gly Tyr Ser Ile Thr Ser Asp
            20                  25                  30

Phe Ala Trp Asn Trp Ile Arg Gln Phe Pro Gly Asn Lys Leu Glu Trp
        35                  40                  45

Met Gly Tyr Ile Ser Tyr Ser Gly Asn Thr Arg Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Ile Glu Asp Thr Ala Thr Tyr Tyr Cys
                85                  90                  95

Val Thr Ala Gly Arg Gly Phe Pro Tyr Trp Gly Gln Gly Thr Leu Val
            100                 105                 110

Thr Val Ser Ala
        115


<210> SEQ ID NO 3
<211> LENGTH: 6
<212> TYPE: PRT
<213> ORGANISM: Artificial Sequence
<220> FEATURE:
<223> OTHER INFORMATION: synthesized

<400> SEQUENCE: 3

Ser Asp Phe Ala Trp Asn
1               5
```

-continued

<210> SEQ ID NO 4
<211> LENGTH: 16
<212> TYPE: PRT
<213> ORGANISM: Artificial Sequence
<220> FEATURE:
<223> OTHER INFORMATION: synthesized

<400> SEQUENCE: 4

```
Tyr Ile Ser Tyr Ser Gly Asn Thr Arg Tyr Asn Pro Ser Leu Lys Ser
1               5                   10                  15
```

<210> SEQ ID NO 5
<211> LENGTH: 9
<212> TYPE: PRT
<213> ORGANISM: Artificial Sequence
<220> FEATURE:
<223> OTHER INFORMATION: synthesized

<400> SEQUENCE: 5

```
Val Thr Ala Gly Arg Gly Phe Pro Tyr
1               5
```

<210> SEQ ID NO 6
<211> LENGTH: 324
<212> TYPE: DNA
<213> ORGANISM: Artificial Sequence
<220> FEATURE:
<223> OTHER INFORMATION: synthesized

<400> SEQUENCE: 6

```
gacatcctga tgacccaatc tccatcctcc atgtctgtat ctctgggaga cacagtcagc      60

atcacttgcc attcaagtca ggacattaac agtaatatag ggtggttgca gcagagacca     120

gggaaatcat ttaagggcct gatctatcat ggaaccaact tggacgatga agttccatca     180

aggttcagtg gcagtggatc tggagccgat tattctctca ccatcagcag cctggaatct     240

gaagattttg cagactatta ctgtgtacag tatgctcagt ttccgtggac gttcggtgga     300

ggcaccaagc tggaaatcaa acgt                                            324
```

<210> SEQ ID NO 7
<211> LENGTH: 108
<212> TYPE: PRT
<213> ORGANISM: Artificial Sequence
<220> FEATURE:
<223> OTHER INFORMATION: synthesized

<400> SEQUENCE: 7

```
Asp Ile Leu Met Thr Gln Ser Pro Ser Ser Met Ser Val Ser Leu Gly
1               5                   10                  15

Asp Thr Val Ser Ile Thr Cys His Ser Ser Gln Asp Ile Asn Ser Asn
            20                  25                  30

Ile Gly Trp Leu Gln Gln Arg Pro Gly Lys Ser Phe Lys Gly Leu Ile
        35                  40                  45

Tyr His Gly Thr Asn Leu Asp Asp Glu Val Pro Ser Arg Phe Ser Gly
    50                  55                  60

Ser Gly Ser Gly Ala Asp Tyr Ser Leu Thr Ile Ser Ser Leu Glu Ser
65                  70                  75                  80

Glu Asp Phe Ala Asp Tyr Tyr Cys Val Gln Tyr Ala Gln Phe Pro Trp
                85                  90                  95

Thr Phe Gly Gly Gly Thr Lys Leu Glu Ile Lys Arg
            100                 105
```

-continued

<210> SEQ ID NO 8
<211> LENGTH: 11
<212> TYPE: PRT
<213> ORGANISM: Artificial Sequence
<220> FEATURE:
<223> OTHER INFORMATION: synthesized

<400> SEQUENCE: 8

His Ser Ser Gln Asp Ile Asn Ser Asn Ile Gly
1 5 10

<210> SEQ ID NO 9
<211> LENGTH: 8
<212> TYPE: PRT
<213> ORGANISM: Artificial Sequence
<220> FEATURE:
<223> OTHER INFORMATION: synthesized

<400> SEQUENCE: 9

His Gly Thr Asn Leu Asp Asp Glu
1 5

<210> SEQ ID NO 10
<211> LENGTH: 9
<212> TYPE: PRT
<213> ORGANISM: Artificial Sequence
<220> FEATURE:
<223> OTHER INFORMATION: synthesized

<400> SEQUENCE: 10

Val Gln Tyr Ala Gln Phe Pro Trp Thr
1 5

<210> SEQ ID NO 11
<211> LENGTH: 990
<212> TYPE: DNA
<213> ORGANISM: Artificial Sequence
<220> FEATURE:
<223> OTHER INFORMATION: synthesized

<400> SEQUENCE: 11
gctagcacca agggcccatc ggtcttcccc ctggcaccct cctccaagag cacctctggg 60
ggcacagcgg ccctgggctg cctggtcaag gactacttcc ccgaaccggt gacggtgtcg 120
tggaactcag gcgccctgac cagcggcgtg cacaccttcc cggctgtcct acagtcctca 180
ggactctact ccctcagcag cgtggtgacc gtgccctcca gcagcttggg cacccagacc 240
tacatctgca acgtgaatca caagcccagc aacaccaagg tggacaagag agttgagccc 300
aaatcttgtg acaaaactca cacatgccca ccgtgcccag cacctgaact cctgggggga 360
ccgtcagtct tcctcttccc cccaaaaccc aaggacaccc tcatgatctc ccggacccct 420
gaggtcacat gcgtggtggt ggacgtgagc cacgaagacc ctgaggtcaa gttcaactgg 480
tacgtggacg gcgtggaggt gcataatgcc aagacaaagc cgcgggagga gcagtacaac 540
agcacgtacc gtgtggtcag cgtcctcacc gtcctgcacc aggactggct gaatggcaag 600
gagtacaagt gcaaggtctc caacaaagcc ctcccagccc ccatcgagaa aaccatctcc 660
aaagccaaag ggcagccccg agaaccacag gtgtacaccc tgcccccatc ccgggatgag 720
ctgaccaaga accaggtcag cctgacctgc ctggtcaaag gcttctatcc cagcgacatc 780
gccgtggagt gggagagcaa tgggcagccg gagaacaact acaagaccac gcctcccgtg 840
ctggactccg acggctcctt cttcctctat agcaagctca ccgtggacaa gagcaggtgg 900
cagcagggga acgtcttctc atgctccgtg atgcatgagg ctctgcacaa ccactacacg 960
cagaagagcc tctccctgtc tccgggtaaa 990

<210> SEQ ID NO 12
<211> LENGTH: 330
<212> TYPE: PRT
<213> ORGANISM: Artificial Sequence
<220> FEATURE:
<223> OTHER INFORMATION: synthesized

<400> SEQUENCE: 12

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 13
<211> LENGTH: 321

-continued

<212> TYPE: DNA
<213> ORGANISM: Artificial Sequence
<220> FEATURE:
<223> OTHER INFORMATION: synthesized

<400> SEQUENCE: 13
acggtggctg caccatctgt cttcatcttc ccgccatctg atgagcagtt gaaatctgga 60
actgcctctg ttgtgtgcct gctgaataac ttctatccca gagaggccaa agtacagtgg 120
aaggtggata acgccctcca atcgggtaac tcccaggaga gtgtcacaga gcaggacagc 180
aaggacagca cctacagcct cagcagcacc ctgacgctga gcaaagcaga ctacgagaaa 240
cacaaagtct acgcctgcga agtcacccat cagggcctga gctcgcccgt cacaaagagc 300
ttcaacaggg gagagtgtta g 321

<210> SEQ ID NO 14
<211> LENGTH: 106
<212> TYPE: PRT
<213> ORGANISM: Artificial Sequence
<220> FEATURE:
<223> OTHER INFORMATION: synthesized

<400> SEQUENCE: 14

Thr Val Ala Ala Pro Ser Val Phe Ile Phe Pro Pro Ser Asp Glu Gln
1 5 10 15

Leu Lys Ser Gly Thr Ala Ser Val Val Cys Leu Leu Asn Asn Phe Tyr
20 25 30

Pro Arg Glu Ala Lys Val Gln Trp Lys Val Asp Asn Ala Leu Gln Ser
35 40 45

Gly Asn Ser Gln Glu Ser Val Thr Glu Gln Asp Ser Lys Asp Ser Thr
50 55 60

Tyr Ser Leu Ser Ser Thr Leu Thr Leu Ser Lys Ala Asp Tyr Glu Lys
65 70 75 80

His Lys Val Tyr Ala Cys Glu Val Thr His Gln Gly Leu Ser Ser Pro
85 90 95

Val Thr Lys Ser Phe Asn Arg Gly Glu Cys
100 105

<210> SEQ ID NO 15
<211> LENGTH: 336
<212> TYPE: DNA
<213> ORGANISM: Artificial Sequence
<220> FEATURE:
<223> OTHER INFORMATION: synthesized

<400> SEQUENCE: 15
gaaatcaaac gtacgtgtgt ggctgcacca tctgtcttca tcttcccgcc atctgatgag 60
cagttgaaat ctggaactgc ctctgttgtg tgcctgctga ataacttcta tcccagagag 120
gccaaagtac agtggaaggt ggataacgcc ctccaatcgg gtaactccca ggagagtgtc 180
acagagcagg acagcaagga cagcacctac agcctcagca gcaccctgac gctgagcaaa 240
gcagactacg agaaacacaa agtctacgcc tgcgaagtca cccatcaggg cctgagctcg 300
cccgtcacaa agagcttcaa caggggagag tgttag 336

<210> SEQ ID NO 16
<211> LENGTH: 110
<212> TYPE: PRT
<213> ORGANISM: Artificial Sequence
<220> FEATURE:
<223> OTHER INFORMATION: synthesized

<400> SEQUENCE: 16

```
Glu Ile Lys Arg Thr Cys Val Ala Ala Pro Ser Val Phe Ile Phe Pro
1               5                   10                  15

Pro Ser Asp Glu Gln Leu Lys Ser Gly Thr Ala Ser Val Val Cys Leu
            20                  25                  30

Leu Asn Asn Phe Tyr Pro Arg Glu Ala Lys Val Gln Trp Lys Val Asp
        35                  40                  45

Asn Ala Leu Gln Ser Gly Asn Ser Gln Glu Ser Val Thr Glu Gln Asp
    50                  55                  60

Ser Lys Asp Ser Thr Tyr Ser Leu Ser Ser Thr Leu Thr Leu Ser Lys
65                  70                  75                  80

Ala Asp Tyr Glu Lys His Lys Val Tyr Ala Cys Glu Val Thr His Gln
                85                  90                  95

Gly Leu Ser Ser Pro Val Thr Lys Ser Phe Asn Arg Gly Glu
            100                 105                 110
```

<210> SEQ ID NO 17
<211> LENGTH: 336
<212> TYPE: DNA
<213> ORGANISM: Artificial Sequence
<220> FEATURE:
<223> OTHER INFORMATION: synthesized

<400> SEQUENCE: 17

```
gaaatcaaac gtacggtgtg tgctgcacca tctgtcttca tcttcccgcc atctgatgag     60

cagttgaaat ctggaactgc ctctgttgtg tgcctgctga ataacttcta tcccagagag    120

gccaaagtac agtggaaggt ggataacgcc ctccaatcgg gtaactccca ggagagtgtc    180

acagagcagg acagcaagga cagcacctac agcctcagca gcaccctgac gctgagcaaa    240

gcagactacg agaaacacaa agtctacgcc tgcgaagtca cccatcaggg cctgagctcg    300

cccgtcacaa agagcttcaa caggggagag tgttag                              336
```

<210> SEQ ID NO 18
<211> LENGTH: 111
<212> TYPE: PRT
<213> ORGANISM: Artificial Sequence
<220> FEATURE:
<223> OTHER INFORMATION: synthesized

<400> SEQUENCE: 18

```
Glu Ile Lys Arg Thr Val Cys Ala Ala Pro Ser Val Phe Ile Phe Pro
1               5                   10                  15

Pro Ser Asp Glu Gln Leu Lys Ser Gly Thr Ala Ser Val Val Cys Leu
            20                  25                  30

Leu Asn Asn Phe Tyr Pro Arg Glu Ala Lys Val Gln Trp Lys Val Asp
        35                  40                  45

Asn Ala Leu Gln Ser Gly Asn Ser Gln Glu Ser Val Thr Glu Gln Asp
    50                  55                  60

Ser Lys Asp Ser Thr Tyr Ser Leu Ser Ser Thr Leu Thr Leu Ser Lys
65                  70                  75                  80

Ala Asp Tyr Glu Lys His Lys Val Tyr Ala Cys Glu Val Thr His Gln
                85                  90                  95

Gly Leu Ser Ser Pro Val Thr Lys Ser Phe Asn Arg Gly Glu Cys
            100                 105                 110
```

<210> SEQ ID NO 19

-continued

<211> LENGTH: 60
<212> TYPE: DNA
<213> ORGANISM: Artificial Sequence
<220> FEATURE:
<223> OTHER INFORMATION: synthesized

<400> SEQUENCE: 19
gaaatcaaac gtacggtggc tgcaccatct gtcttcatct tcccgccatc tgatgagcag 60

<210> SEQ ID NO 20
<211> LENGTH: 111
<212> TYPE: PRT
<213> ORGANISM: Artificial Sequence
<220> FEATURE:
<223> OTHER INFORMATION: synthesized

<400> SEQUENCE: 20

```
Glu Ile Lys Arg Thr Val Ala Ala Pro Ser Val Phe Ile Phe Pro Pro
1               5                   10                  15

Ser Asp Glu Gln Leu Lys Ser Gly Thr Ala Ser Val Val Cys Leu Leu
            20                  25                  30

Asn Asn Phe Tyr Pro Cys Arg Glu Ala Lys Val Gln Trp Lys Val Asp
        35                  40                  45

Asn Ala Leu Gln Ser Gly Asn Ser Gln Glu Ser Val Thr Glu Gln Asp
    50                  55                  60

Ser Lys Asp Ser Thr Tyr Ser Leu Ser Ser Thr Leu Thr Leu Ser Lys
65                  70                  75                  80

Ala Asp Tyr Glu Lys His Lys Val Tyr Ala Cys Glu Val Thr His Gln
                85                  90                  95

Gly Leu Ser Ser Pro Val Thr Lys Ser Phe Asn Arg Gly Glu Cys
            100                 105                 110
```

<210> SEQ ID NO 21
<211> LENGTH: 993
<212> TYPE: DNA
<213> ORGANISM: Artificial Sequence
<220> FEATURE:
<223> OTHER INFORMATION: synthesized

<400> SEQUENCE: 21

```
gctagcacca agggcccatc ggtcttcccc ctggcaccct cctccaagag cacctctggg     60

ggcacagcgg ccctgggctg cctggtcaag gactacttcc ccgaaccggt gacggtgtcg    120

tggaactcag gcgccctgac cagcggcgtg cacaccttcc cggctgtcct acagtcctca    180

ggactctact ccctcagcag cgtggtgacc gtgccctcca gcagcttggg cacccagacc    240

tacatctgca acgtgaatca caagcccagc aacaccaagg tggacaagag agttgagccc    300

aaatcttgtg acaaaactca cacatgccca ccgtgcccag cacctgaatt cctgggggga    360

ccgtcagtct tcctcttccc cccaaaaccc aaggacaccc tcatgatctc ccggacccct    420

tgtgaggtca catgcgtggt ggtggacgtg agccacgaag accctgaggt caagttcaac    480

tggtacgtgg acggcgtgga ggtgcataat gccaagacaa agccgcggga ggagcagtac    540

aacagcacgt accgtgtggt cagcgtcctc accgtcctgc accaggactg gctgaatggc    600

aaggagtaca agtgcaaggt ctccaacaaa gccctcccag cccccatcga gaaaaccatc    660

tccaaagcca aagggcagcc ccgagaacca caggtgtaca ccctgccccc atcccgggat    720

gagctgacca agaaccaggt cagcctgacc tgcctggtca aaggcttcta tcccagcgac    780

atcgccgtgg agtgggagag caatgggcag ccggagaaca actacaagac cacgcctccc    840
```

-continued

```
gtgctggact ccgacggctc cttcttcctc tatagcaagc tcaccgtgga caagagcagg    900

tggcagcagg ggaacgtctt ctcatgctcc gtgatgcatg aggctctgca caaccactac    960

acgcagaaga gcctctccct gtctccgggt taa                                 993


<210> SEQ ID NO 22
<211> LENGTH: 330
<212> TYPE: PRT
<213> ORGANISM: Artificial Sequence
<220> FEATURE:
<223> OTHER INFORMATION: synthesized

<400> SEQUENCE: 22

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Phe Leu Gly Gly Pro Ser Val Phe Leu Phe Pro Pro
        115                 120                 125

Lys Pro Lys Asp Thr Leu Met Ile Ser Arg Thr Pro Cys Glu Val Thr
    130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Asp
225                 230                 235                 240

Glu Leu Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly
                325                 330
```

-continued

<210> SEQ ID NO 23
<211> LENGTH: 993
<212> TYPE: DNA
<213> ORGANISM: Artificial Sequence
<220> FEATURE:
<223> OTHER INFORMATION: synthesized

<400> SEQUENCE: 23
gctagcacca agggcccatc ggtcttcccc ctggcaccct cctccaagag cacctctggg 60
ggcacagcgg ccctgggctg cctggtcaag gactacttcc ccgaaccggt gacggtgtcg 120
tggaactcag gcgccctgac cagcggcgtg cacaccttcc cggctgtcct acagtcctca 180
ggactctact ccctcagcag cgtggtgacc gtgccctcca gcagcttggg cacccagacc 240
tacatctgca acgtgaatca caagcccagc aacaccaagg tggacaagag agttgagccc 300
aaatcttgtg acaaaactca cacatgccca ccgtgcccag cacctgaatt cctgggggga 360
ccgtcagtct tcctcttccc cccaaaaccc aaggacaccc tcatgatctc ccggacccct 420
gagtgtgtca catgcgtggt ggtggacgtg agccacgaag accctgaggt caagttcaac 480
tggtacgtgg acggcgtgga ggtgcataat gccaagacaa agccgcggga ggagcagtac 540
aacagcacgt accgtgtggt cagcgtcctc accgtcctgc accaggactg gctgaatggc 600
aaggagtaca agtgcaaggt ctccaacaaa gccctcccag cccccatcga gaaaaccatc 660
tccaaagcca aagggcagcc ccgagaacca caggtgtaca ccctgccccc atcccgggat 720
gagctgacca agaaccaggt cagcctgacc tgcctggtca aaggcttcta tcccagcgac 780
atcgccgtgg agtgggagag caatgggcag ccggagaaca actacaagac cacgcctccc 840
gtgctggact ccgacggctc cttcttcctc tatagcaagc tcaccgtgga caagagcagg 900
tggcagcagg ggaacgtctt ctcatgctcc gtgatgcatg aggctctgca caaccactac 960
acgcagaaga gcctctccct gtctccgggt taa 993

<210> SEQ ID NO 24
<211> LENGTH: 330
<212> TYPE: PRT
<213> ORGANISM: Artificial Sequence
<220> FEATURE:
<223> OTHER INFORMATION: synthesized

<400> SEQUENCE: 24

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Arg Val Glu Pro Lys Ser Cys Asp Lys Thr His Thr Cys Pro Pro Cys
100 105 110

Pro Ala Pro Glu Phe Leu Gly Gly Pro Ser Val Phe Leu Phe Pro Pro
115 120 125

Lys Pro Lys Asp Thr Leu Met Ile Ser Arg Thr Pro Glu Cys Val Thr

-continued

```
    130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Asp
225                 230                 235                 240

Glu Leu Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly
                325                 330


<210> SEQ ID NO 25
<211> LENGTH: 993
<212> TYPE: DNA
<213> ORGANISM: Artificial Sequence
<220> FEATURE:
<223> OTHER INFORMATION: synthesized

<400> SEQUENCE: 25

gctagcacca agggcccatc ggtcttcccc ctggcaccct cctccaagag cacctctggg     60

ggcacagcgg ccctgggctg cctggtcaag gactacttcc ccgaaccggt gacggtgtcg    120

tggaactcag gcgccctgac cagcggcgtg cacaccttcc cggctgtcct acagtcctca    180

ggactctact ccctcagcag cgtggtgacc gtgccctcca gcagcttggg cacccagacc    240

tacatctgca acgtgaatca caagcccagc aacaccaagg tggacaagag agttgagccc    300

aaatcttgtg acaaaactca cacatgccca ccgtgcccag cacctgaatt cctgggggga    360

ccgtcagtct tcctcttccc cccaaaaccc aaggacaccc tcatgatctc ccggacccct    420

gaggtcacat gctgtgtggt ggtggacgtg agccacgaag accctgaggt caagttcaac    480

tggtacgtgg acggcgtgga ggtgcataat gccaagacaa agccgcggga ggagcagtac    540

aacagcacgt accgtgtggt cagcgtcctc accgtcctgc accaggactg gctgaatggc    600

aaggagtaca agtgcaaggt ctccaacaaa gccctcccag cccccatcga gaaaaccatc    660

tccaaagcca aagggcagcc ccgagaacca caggtgtaca ccctgccccc atcccgggat    720

gagctgacca agaaccaggt cagcctgacc tgcctggtca aaggcttcta tcccagcgac    780

atcgccgtgg agtgggagag caatgggcag ccggagaaca actacaagac cacgcctccc    840

gtgctggact ccgacggctc cttcttcctc tatagcaagc tcaccgtgga caagagcagg    900

tggcagcagg ggaacgtctt ctcatgctcc gtgatgcatg aggctctgca caaccactac    960
```

acgcagaaga gcctctccct gtctccgggt taa 993

<210> SEQ ID NO 26
<211> LENGTH: 330
<212> TYPE: PRT
<213> ORGANISM: Artificial Sequence
<220> FEATURE:
<223> OTHER INFORMATION: synthesized

<400> SEQUENCE: 26

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Phe Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Asp
225                 230                 235                 240

Glu Leu Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly
                325                 330
```

<210> SEQ ID NO 27
<211> LENGTH: 993

<212> TYPE: DNA
<213> ORGANISM: Artificial Sequence
<220> FEATURE:
<223> OTHER INFORMATION: synthesized

<400> SEQUENCE: 27
gctagcacca agggcccatc ggtcttcccc ctggcaccct cctccaagag cacctctggg 60
ggcacagcgg ccctgggctg cctggtcaag gactacttcc ccgaaccggt gacggtgtcg 120
tggaactcag gcgccctgac cagcggcgtg cacaccttcc cggctgtcct acagtcctca 180
ggactctact ccctcagcag cgtggtgacc gtgccctcca gcagcttggg cacccagacc 240
tacatctgca acgtgaatca caagcccagc aacaccaagg tggacaagag agttgagccc 300
aaatcttgtg acaaaactca cacatgccca ccgtgcccag cacctgaatt cctgggggga 360
ccgtcagtct tcctcttccc cccaaaaccc aaggacaccc tcatgatctc ccggacccct 420
gaggtcacat gcgtgtgtgt ggtggacgtg agccacgaag accctgaggt caagttcaac 480
tggtacgtgg acggcgtgga ggtgcataat gccaagacaa agccgcggga ggagcagtac 540
aacagcacgt accgtgtggt cagcgtcctc accgtcctgc accaggactg gctgaatggc 600
aaggagtaca agtgcaaggt ctccaacaaa gccctcccag cccccatcga gaaaaccatc 660
tccaaagcca aagggcagcc ccgagaacca caggtgtaca ccctgccccc atcccgggat 720
gagctgacca agaaccaggt cagcctgacc tgcctggtca aaggcttcta tcccagcgac 780
atcgccgtgg agtgggagag caatgggcag ccggagaaca actacaagac cacgcctccc 840
gtgctggact ccgacggctc cttcttcctc tatagcaagc tcaccgtgga caagagcagg 900
tggcagcagg ggaacgtctt ctcatgctcc gtgatgcatg aggctctgca caaccactac 960
acgcagaaga gcctctccct gtctccgggt taa 993

<210> SEQ ID NO 28
<211> LENGTH: 330
<212> TYPE: PRT
<213> ORGANISM: Artificial Sequence
<220> FEATURE:
<223> OTHER INFORMATION: synthesized

<400> SEQUENCE: 28

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Phe Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Cys Val Val Asp Val Ser His Glu Asp Pro Glu Val Lys Phe Asn

-continued

```
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Asp
225                 230                 235                 240

Glu Leu Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly
                325                 330
```

<210> SEQ ID NO 29
<211> LENGTH: 993
<212> TYPE: DNA
<213> ORGANISM: Artificial Sequence
<220> FEATURE:
<223> OTHER INFORMATION: synthesized

<400> SEQUENCE: 29

```
gctagcacca agggcccatc ggtcttcccc ctggcaccct cctccaagag cacctctggg     60

ggcacagcgg ccctgggctg cctggtcaag gactacttcc ccgaaccggt gacggtgtcg    120

tggaactcag gcgccctgac cagcggcgtg cacaccttcc cggctgtcct acagtcctca    180

ggactctact ccctcagcag cgtggtgacc gtgccctcca gcagcttggg cacccagacc    240

tacatctgca acgtgaatca caagcccagc aacaccaagg tggacaagag agttgagccc    300

aaatcttgtg acaaaactca cacatgccca ccgtgcccag cacctgaatt cctgggggga    360

ccgtcagtct tcctcttccc cccaaaaccc aaggacaccc tcatgatctc ccggacccct    420

gaggtcacat gcgtggtggt ggacgtgagc cacgaagacc ctgaggtcaa gttcaactgg    480

tacgtggacg gcgtggaggt gcataatgcc aagacaaagc cgcgggagga gcagtacaac    540

agcacgtacc gtgtggtcag cgtcctcacc gtcctgcacc aggactggct gaatggcaag    600

gagtacaagt gcaaggtctc caacaaagcc ctcccagccc ccatcgagaa aaccatctcc    660

aaagccaaag ggcagccccg agaaccacag gtgtacaccc tgcccccatc ccgggatgag    720

tgtctgacca agaaccaggt cagcctgacc tgcctggtca aaggcttcta tcccagcgac    780

atcgccgtgg agtgggagag caatgggcag ccggagaaca actacaagac cacgcctccc    840

gtgctggact ccgacggctc cttcttcctc tatagcaagc tcaccgtgga caagagcagg    900

tggcagcagg ggaacgtctt ctcatgctcc gtgatgcatg aggctctgca caaccactac    960

acgcagaaga gcctctccct gtctccgggt taa                                 993
```

<210> SEQ ID NO 30
<211> LENGTH: 330
<212> TYPE: PRT
<213> ORGANISM: Artificial Sequence
<220> FEATURE:
<223> OTHER INFORMATION: synthesized

<400> SEQUENCE: 30

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Phe Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Cys Leu Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly
                325                 330
```

<210> SEQ ID NO 31
<211> LENGTH: 993
<212> TYPE: DNA
<213> ORGANISM: Artificial Sequence
<220> FEATURE:

-continued

<223> OTHER INFORMATION: synthesized

<400> SEQUENCE: 31
gctagcacca agggcccatc ggtcttcccc ctggcaccct cctccaagag cacctctggg 60
ggcacagcgg ccctgggctg cctggtcaag gactacttcc ccgaaccggt gacggtgtcg 120
tggaactcag gcgccctgac cagcggcgtg cacaccttcc cggctgtcct acagtcctca 180
ggactctact ccctcagcag cgtggtgacc gtgccctcca gcagcttggg cacccagacc 240
tacatctgca acgtgaatca caagcccagc aacaccaagg tggacaagag agttgagccc 300
aaatcttgtg acaaaactca cacatgccca ccgtgcccag cacctgaatt cctgggggga 360
ccgtcagtct tcctcttccc cccaaaaccc aaggacaccc tcatgatctc ccggacccct 420
gaggtcacat gcgtggtggt ggacgtgagc cacgaagacc ctgaggtcaa gttcaactgg 480
tacgtggacg gcgtggaggt gcataatgcc aagacaaagc cgcgggagga gcagtacaac 540
agcacgtacc gtgtggtcag cgtcctcacc gtcctgcacc aggactggct gaatggcaag 600
gagtacaagt gcaaggtctc caacaaagcc ctcccagccc ccatcgagaa aaccatctcc 660
aaagccaaag ggcagccccg agaaccacag gtgtacaccc tgcccccatc ccgggatgag 720
ctgtgtacca agaaccaggt cagcctgacc tgcctggtca aaggcttcta tcccagcgac 780
atcgccgtgg agtgggagag caatgggcag ccggagaaca actacaagac cacgcctccc 840
gtgctggact ccgacggctc cttcttcctc tatagcaagc tcaccgtgga caagagcagg 900
tggcagcagg ggaacgtctt ctcatgctcc gtgatgcatg aggctctgca caaccactac 960
acgcagaaga gcctctccct gtctccgggt taa 993

<210> SEQ ID NO 32
<211> LENGTH: 330
<212> TYPE: PRT
<213> ORGANISM: Artificial Sequence
<220> FEATURE:
<223> OTHER INFORMATION: synthesized

<400> SEQUENCE: 32

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Arg Val Glu Pro Lys Ser Cys Asp Lys Thr His Thr Cys Pro Pro Cys
100 105 110

Pro Ala Pro Glu Phe Leu Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu

-continued

```
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Cys Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly
                325                 330


<210> SEQ ID NO 33
<211> LENGTH: 993
<212> TYPE: DNA
<213> ORGANISM: Artificial Sequence
<220> FEATURE:
<223> OTHER INFORMATION: synthesized

<400> SEQUENCE: 33

gctagcacca agggcccatc ggtcttcccc ctggcaccct cctccaagag cacctctggg      60

ggcacagcgg ccctgggctg cctggtcaag gactacttcc ccgaaccggt gacggtgtcg     120

tggaactcag gcgccctgac cagcggcgtg cacaccttcc cggctgtcct acagtcctca     180

ggactctact ccctcagcag cgtggtgacc gtgccctcca gcagcttggg cacccagacc     240

tacatctgca acgtgaatca caagcccagc aacaccaagg tggacaagag agttgagccc     300

aaatcttgtg acaaaactca cacatgccca ccgtgcccag cacctgaatt cctgggggga     360

ccgtcagtct tcctcttccc cccaaaaccc aaggacaccc tcatgatctc ccggacccct     420

gaggtcacat gcgtggtggt ggacgtgagc cacgaagacc ctgaggtcaa gttcaactgg     480

tacgtggacg gcgtggaggt gcataatgcc aagacaaagc cgcgggagga gcagtacaac     540

agcacgtacc gtgtggtcag cgtcctcacc gtcctgcacc aggactggct gaatggcaag     600

gagtacaagt gcaaggtctc caacaaagcc ctcccagccc ccatcgagaa aaccatctcc     660

aaagccaaag ggcagccccg agaaccacag gtgtacaccc tgcccccatc ccgggatgag     720

ctgaccaagt gtaaccaggt cagcctgacc tgcctggtca aaggcttcta tcccagcgac     780

atcgccgtgg agtgggagag caatgggcag ccggagaaca actacaagac cacgcctccc     840

gtgctggact ccgacggctc cttcttcctc tatagcaagc tcaccgtgga caagagcagg     900

tggcagcagg ggaacgtctt ctcatgctcc gtgatgcatg aggctctgca caaccactac     960

acgcagaaga gcctctccct gtctccgggt taa                                  993


<210> SEQ ID NO 34
<211> LENGTH: 330
```

<212> TYPE: PRT
<213> ORGANISM: Artificial Sequence
<220> FEATURE:
<223> OTHER INFORMATION: synthesized

<400> SEQUENCE: 34

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Phe Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Cys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly
                325                 330
```

<210> SEQ ID NO 35
<211> LENGTH: 993
<212> TYPE: DNA
<213> ORGANISM: Artificial Sequence
<220> FEATURE:
<223> OTHER INFORMATION: synthesized

<400> SEQUENCE: 35

-continued

```
gctagcacca agggcccatc ggtcttcccc ctggcaccct cctccaagag cacctctggg     60

ggcacagcgg ccctgggctg cctggtcaag gactacttcc ccgaaccggt gacggtgtcg    120

tggaactcag gcgccctgac cagcggcgtg cacaccttcc cggctgtcct acagtcctca    180

ggactctact ccctcagcag cgtggtgacc gtgccctcca gcagcttggg cacccagacc    240

tacatctgca acgtgaatca caagcccagc aacaccaagg tggacaagag agttgagccc    300

aaatcttgtg acaaaactca cacatgccca ccgtgcccag cacctgaatt cctgggggga    360

ccgtcagtct tcctcttccc cccaaaaccc aaggacaccc tcatgatctc ccggacccct    420

gaggtcacat gcgtggtggt ggacgtgagc cacgaagacc ctgaggtcaa gttcaactgg    480

tacgtggacg gcgtggaggt gcataatgcc aagacaaagc cgcgggagga gcagtacaac    540

agcacgtacc gtgtggtcag cgtcctcacc gtcctgcacc aggactggct gaatggcaag    600

gagtacaagt gcaaggtctc caacaaagcc ctcccagccc ccatcgagaa aaccatctcc    660

aaagccaaag ggcagccccg agaaccacag gtgtacaccc tgcccccatc ccgggatgag    720

ctgaccaaga accaggtcag cctgacctgc ctggtcaaag gcttctatcc cagcgacatc    780

gccgtggagt ggtgtgagag caatgggcag ccggagaaca actacaagac cacgcctccc    840

gtgctggact ccgacggctc cttcttcctc tatagcaagc tcaccgtgga caagagcagg    900

tggcagcagg ggaacgtctt ctcatgctcc gtgatgcatg aggctctgca caaccactac    960

acgcagaaga gcctctccct gtctccgggt taa                                 993


<210> SEQ ID NO 36
<211> LENGTH: 330
<212> TYPE: PRT
<213> ORGANISM: Artificial Sequence
<220> FEATURE:
<223> OTHER INFORMATION: synthesized

<400> SEQUENCE: 36

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Phe Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
```

-continued

```
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Cys Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly
                325                 330
```

<210> SEQ ID NO 37
<211> LENGTH: 993
<212> TYPE: DNA
<213> ORGANISM: Artificial Sequence
<220> FEATURE:
<223> OTHER INFORMATION: synthesized

<400> SEQUENCE: 37

```
gctagcacca agggcccatc ggtcttcccc ctggcaccct cctccaagag cacctctggg      60

ggcacagcgg ccctgggctg cctggtcaag gactacttcc ccgaaccggt gacggtgtcg     120

tggaactcag gcgccctgac cagcggcgtg cacaccttcc cggctgtcct acagtcctca     180

ggactctact ccctcagcag cgtggtgacc gtgccctcca gcagcttggg cacccagacc     240

tacatctgca acgtgaatca caagcccagc aacaccaagg tggacaagag agttgagccc     300

aaatcttgtg acaaaactca cacatgccca ccgtgcccag cacctgaatt cctgggggga     360

ccgtcagtct tcctcttccc cccaaaaccc aaggacaccc tcatgatctc ccggacccct     420

gaggtcacat gcgtggtggt ggacgtgagc cacgaagacc ctgaggtcaa gttcaactgg     480

tacgtggacg gcgtggaggt gcataatgcc aagacaaagc cgcgggagga gcagtacaac     540

agcacgtacc gtgtggtcag cgtcctcacc gtcctgcacc aggactggct gaatggcaag     600

gagtacaagt gcaaggtctc caacaaagcc ctcccagccc ccatcgagaa aaccatctcc     660

aaagccaaag ggcagccccg agaaccacag gtgtacaccc tgcccccatc ccgggatgag     720

ctgaccaaga accaggtcag cctgacctgc ctggtcaaag gcttctatcc cagcgacatc     780

gccgtggagt gggagtgtag caatgggcag ccggagaaca actacaagac cacgcctccc     840

gtgctggact ccgacggctc cttcttcctc tatagcaagc tcaccgtgga caagagcagg     900

tggcagcagg ggaacgtctt ctcatgctcc gtgatgcatg aggctctgca caaccactac     960

acgcagaaga gcctctccct gtctccgggt taa                                  993
```

<210> SEQ ID NO 38
<211> LENGTH: 330
<212> TYPE: PRT
<213> ORGANISM: Artificial Sequence
<220> FEATURE:

<223> OTHER INFORMATION: synthesized

<400> SEQUENCE: 38

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Phe Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Cys Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly
                325                 330
```

<210> SEQ ID NO 39
<211> LENGTH: 993
<212> TYPE: DNA
<213> ORGANISM: Artificial Sequence
<220> FEATURE:
<223> OTHER INFORMATION: synthesized

<400> SEQUENCE: 39

```
gctagcacca agggcccatc ggtcttcccc ctggcaccct cctccaagag cacctctggg      60
```

-continued

```
ggcacagcgg ccctgggctg cctggtcaag gactacttcc ccgaaccggt gacggtgtcg    120

tggaactcag gcgccctgac cagcggcgtg cacaccttcc cggctgtcct acagtcctca    180

ggactctact ccctcagcag cgtggtgacc gtgccctcca gcagcttggg cacccagacc    240

tacatctgca acgtgaatca caagcccagc aacaccaagg tggacaagag agttgagccc    300

aaatcttgtg acaaaactca cacatgccca ccgtgcccag cacctgaatt cctgggggga    360

ccgtcagtct tcctcttccc cccaaaaccc aaggacaccc tcatgatctc ccggacccct    420

gaggtcacat gcgtggtggt ggacgtgagc cacgaagacc ctgaggtcaa gttcaactgg    480

tacgtggacg gcgtggaggt gcataatgcc aagacaaagc cgcgggagga gcagtacaac    540

agcacgtacc gtgtggtcag cgtcctcacc gtcctgcacc aggactggct gaatggcaag    600

gagtacaagt gcaaggtctc caacaaagcc ctcccagccc ccatcgagaa aaccatctcc    660

aaagccaaag ggcagccccg agaaccacag gtgtacaccc tgcccccatc ccgggatgag    720

ctgaccaaga accaggtcag cctgacctgc ctggtcaaag gcttctatcc cagcgacatc    780

gccgtggagt gggagagcaa tgggcagccg gagaactgta actacaagac cacgcctccc    840

gtgctggact ccgacggctc cttcttcctc tatagcaagc tcaccgtgga caagagcagg    900

tggcagcagg ggaacgtctt ctcatgctcc gtgatgcatg aggctctgca caaccactac    960

acgcagaaga gcctctccct gtctccgggt taa                                 993
```

<210> SEQ ID NO 40
<211> LENGTH: 330
<212> TYPE: PRT
<213> ORGANISM: Artificial Sequence
<220> FEATURE:
<223> OTHER INFORMATION: synthesized

<400> SEQUENCE: 40

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Phe Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
```

```
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Cys Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly
                325                 330
```

<210> SEQ ID NO 41
<211> LENGTH: 993
<212> TYPE: DNA
<213> ORGANISM: Artificial Sequence
<220> FEATURE:
<223> OTHER INFORMATION: synthesized

<400> SEQUENCE: 41

```
gctagcacca agggcccatc ggtcttcccc ctggcaccct cctccaagag cacctctggg     60

ggcacagcgg ccctgggctg cctggtcaag gactacttcc ccgaaccggt gacggtgtcg    120

tggaactcag gcgccctgac cagcggcgtg cacaccttcc cggctgtcct acagtcctca    180

ggactctact ccctcagcag cgtggtgacc gtgccctcca gcagcttggg cacccagacc    240

tacatctgca acgtgaatca caagcccagc aacaccaagg tggacaagag agttgagccc    300

aaatcttgtg acaaaactca cacatgccca ccgtgcccag cacctgaatt cctgggggga    360

ccgtcagtct tcctcttccc cccaaaaccc aaggacaccc tcatgatctc ccggacccct    420

gaggtcacat gcgtggtggt ggacgtgagc cacgaagacc ctgaggtcaa gttcaactgg    480

tacgtggacg gcgtggaggt gcataatgcc aagacaaagc cgcgggagga gcagtacaac    540

agcacgtacc gtgtggtcag cgtcctcacc gtcctgcacc aggactggct gaatggcaag    600

gagtacaagt gcaaggtctc caacaaagcc ctcccagccc ccatcgagaa aaccatctcc    660

aaagccaaag ggcagccccg agaaccacag gtgtacaccc tgcccccatc ccgggatgag    720

ctgaccaaga accaggtcag cctgacctgc ctggtcaaag gcttctatcc cagcgacatc    780

gccgtggagt gggagagcaa tgggcagccg gagaacaact gttacaagac cacgcctccc    840

gtgctggact ccgacggctc cttcttcctc tatagcaagc tcaccgtgga caagagcagg    900

tggcagcagg ggaacgtctt ctcatgctcc gtgatgcatg aggctctgca caaccactac    960

acgcagaaga gcctctccct gtctccgggt taa                                 993
```

<210> SEQ ID NO 42
<211> LENGTH: 330
<212> TYPE: PRT
<213> ORGANISM: Artificial Sequence
<220> FEATURE:
<223> OTHER INFORMATION: synthesized

<400> SEQUENCE: 42

-continued

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Phe Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Cys Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly
                325                 330
```

<210> SEQ ID NO 43
<211> LENGTH: 993
<212> TYPE: DNA
<213> ORGANISM: Artificial Sequence
<220> FEATURE:
<223> OTHER INFORMATION: synthesized

<400> SEQUENCE: 43

```
gctagcacca agggcccatc ggtcttcccc ctggcaccct cctccaagag cacctctggg      60

ggcacagcgg ccctgggctg cctggtcaag gactacttcc ccgaaccggt gacggtgtcg     120

tggaactcag gcgccctgac cagcggcgtg cacaccttcc cggctgtcct acagtcctca     180
```

```
ggactctact ccctcagcag cgtggtgacc gtgccctcca gcagcttggg cacccagacc    240

tacatctgca acgtgaatca caagcccagc aacaccaagg tggacaagag agttgagccc    300

aaatcttgtg acaaaactca cacatgccca ccgtgcccag cacctgaatt cctgggggga    360

ccgtcagtct tcctcttccc cccaaaaccc aaggacaccc tcatgatctc ccggacccct    420

gaggtcacat gcgtggtggt ggacgtgagc cacgaagacc ctgaggtcaa gttcaactgg    480

tacgtggacg gcgtggaggt gcataatgcc aagacaaagc cgcgggagga gcagtacaac    540

agcacgtacc gtgtggtcag cgtcctcacc gtcctgcacc aggactggct gaatggcaag    600

gagtacaagt gcaaggtctc caacaaagcc ctcccagccc ccatcgagaa aaccatctcc    660

aaagccaaag ggcagccccg agaaccacag gtgtacaccc tgcccccatc ccgggatgag    720

ctgaccaaga accaggtcag cctgacctgc ctggtcaaag gcttctatcc cagcgacatc    780

gccgtggagt gggagagcaa tgggcagccg gagaacaact acaagaccac gcctcccgtg    840

ctggactccg acggctcctt cttcctctat agcaagctca ccgtggactg taagagcagg    900

tggcagcagg ggaacgtctt ctcatgctcc gtgatgcatg aggctctgca caaccactac    960

acgcagaaga gcctctccct gtctccgggt taa                                 993
```

<210> SEQ ID NO 44
<211> LENGTH: 330
<212> TYPE: PRT
<213> ORGANISM: Artificial Sequence
<220> FEATURE:
<223> OTHER INFORMATION: synthesized

<400> SEQUENCE: 44

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Phe Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
```

```
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Cys Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly
                325                 330


<210> SEQ ID NO 45
<211> LENGTH: 11
<212> TYPE: PRT
<213> ORGANISM: Artificial Sequence
<220> FEATURE:
<223> OTHER INFORMATION: synthesized

<400> SEQUENCE: 45

Glu Ile Lys Arg Thr Cys Val Ala Ala Pro Ser
1               5                   10


<210> SEQ ID NO 46
<211> LENGTH: 11
<212> TYPE: PRT
<213> ORGANISM: Artificial Sequence
<220> FEATURE:
<223> OTHER INFORMATION: synthesized

<400> SEQUENCE: 46

Ile Lys Arg Thr Val Cys Ala Ala Pro Ser Val
1               5                   10


<210> SEQ ID NO 47
<211> LENGTH: 11
<212> TYPE: PRT
<213> ORGANISM: Artificial Sequence
<220> FEATURE:
<223> OTHER INFORMATION: synthesized

<400> SEQUENCE: 47

Asn Asn Phe Tyr Pro Cys Arg Glu Ala Lys Val
1               5                   10


<210> SEQ ID NO 48
<211> LENGTH: 11
<212> TYPE: PRT
<213> ORGANISM: Artificial Sequence
<220> FEATURE:
<223> OTHER INFORMATION: synthesized

<400> SEQUENCE: 48

Ile Ser Arg Thr Pro Cys Glu Val Thr Cys Val
1               5                   10


<210> SEQ ID NO 49
<211> LENGTH: 11
<212> TYPE: PRT
```

<213> ORGANISM: Artificial Sequence
<220> FEATURE:
<223> OTHER INFORMATION: synthesized

<400> SEQUENCE: 49

Ser Arg Thr Pro Glu Cys Val Thr Cys Val Val
1 5 10

<210> SEQ ID NO 50
<211> LENGTH: 11
<212> TYPE: PRT
<213> ORGANISM: Artificial Sequence
<220> FEATURE:
<223> OTHER INFORMATION: synthesized

<400> SEQUENCE: 50

Pro Glu Val Thr Cys Cys Val Val Val Asp Val
1 5 10

<210> SEQ ID NO 51
<211> LENGTH: 11
<212> TYPE: PRT
<213> ORGANISM: Artificial Sequence
<220> FEATURE:
<223> OTHER INFORMATION: synthesized

<400> SEQUENCE: 51

Glu Val Thr Cys Val Cys Val Val Asp Val Ser
1 5 10

<210> SEQ ID NO 52
<211> LENGTH: 11
<212> TYPE: PRT
<213> ORGANISM: Artificial Sequence
<220> FEATURE:
<223> OTHER INFORMATION: synthesized

<400> SEQUENCE: 52

Pro Ser Arg Asp Glu Cys Leu Thr Lys Asn Gln
1 5 10

<210> SEQ ID NO 53
<211> LENGTH: 11
<212> TYPE: PRT
<213> ORGANISM: Artificial Sequence
<220> FEATURE:
<223> OTHER INFORMATION: Synthesized

<400> SEQUENCE: 53

Ser Arg Asp Glu Leu Cys Thr Lys Asn Gln Val
1 5 10

<210> SEQ ID NO 54
<211> LENGTH: 11
<212> TYPE: PRT
<213> ORGANISM: Artificial Sequence
<220> FEATURE:
<223> OTHER INFORMATION: Synthesized

<400> SEQUENCE: 54

Asp Glu Leu Thr Lys Cys Asn Gln Val Ser Leu
1 5 10

<210> SEQ ID NO 55
<211> LENGTH: 11
<212> TYPE: PRT
<213> ORGANISM: Artificial Sequence -continued
<220> FEATURE:
<223> OTHER INFORMATION: Synthesized

<400> SEQUENCE: 55

Ile Ala Val Glu Trp Cys Glu Ser Asn Gly Gln
1 5 10

<210> SEQ ID NO 56
<211> LENGTH: 11
<212> TYPE: PRT
<213> ORGANISM: Artificial Sequence
<220> FEATURE:
<223> OTHER INFORMATION: Synthesized

<400> SEQUENCE: 56

Ala Val Glu Trp Glu Cys Ser Asn Gly Gln Pro
1 5 10

<210> SEQ ID NO 57
<211> LENGTH: 11
<212> TYPE: PRT
<213> ORGANISM: Artificial Sequence
<220> FEATURE:
<223> OTHER INFORMATION: Synthesized

<400> SEQUENCE: 57

Gly Gln Pro Glu Asn Cys Asn Tyr Lys Thr Thr
1 5 10

<210> SEQ ID NO 58
<211> LENGTH: 11
<212> TYPE: PRT
<213> ORGANISM: Artificial Sequence
<220> FEATURE:
<223> OTHER INFORMATION: Synthesized

<400> SEQUENCE: 58

Gln Pro Glu Asn Asn Cys Tyr Lys Thr Thr Pro
1 5 10

<210> SEQ ID NO 59
<211> LENGTH: 11
<212> TYPE: PRT
<213> ORGANISM: Artificial Sequence
<220> FEATURE:
<223> OTHER INFORMATION: Synthesized

<400> SEQUENCE: 59

Lys Leu Thr Val Asp Cys Lys Ser Arg Trp Gln
1 5 10

SCREENING OF FIXED-POINT COUPLING SITES OF CYSTEINE-MODIFIED ANTIBODY-TOXIN CONJUGATE (TDC)

TECHNICAL FIELD

The present invention relates to a compound as well as methods for the preparation and applications thereof, and in particular relates to a class of cysteine-modified antibody-toxin conjugates (TDCs) and to methods for the preparation and applications thereof.

TECHNICAL BACKGROUND

Antibody drug conjugates (ADCs) represent a currently hot area in the field of targeted therapy, with two drugs already approved in the U.S., Adcetris and Kadcyla, showing good clinical efficacy, and more than 50 ADCs are currently being investigated as part of clinical phase studies. The novel cysteine-modified antibody-toxin conjugate (TDC) disclosed in this patent has the advantage of better drug homogeneity and fewer side effects compared to non-fixed-point coupled ADCs, and have been shown to perform significantly better than non-fixed-point coupled ADCs in preclinical studies.

SUMMARY OF THE INVENTION

For the cysteine-modified antibody-toxin conjugate (TDC) constituted by the present invention, corresponding cysteine insertion sites comprise one or more sites selected from the following 15 insertion sites: Light Chain Position 110 (Kabat number, with amino acid sequence EIKRTCVAAPS (SEQ ID NO: 45)), Light Chain Position 111 (Kabat number, with amino acid sequence IKRTVCAAPSV (SEQ ID NO:46)), Light Chain Position 142 (Kabat number, with amino acid sequence NNFYPCREAKV (SEQ ID NO: 47)), Heavy Chain Position 254 (with amino acid sequence ISRTPCEVTCV (SEQ ID NO: 48)), Heavy Chain Position 255 (with amino acid sequence SRTPECVTCVV (SEQ ID NO: 49)), Heavy Chain Position 258 (with amino acid sequence PEVTCCVVVDV (SEQ ID NO: 50)), Heavy Chain Position 259 (with amino acid sequence EVTCVCVVDVS (SEQ ID NO: 51)), Heavy Chain Position 354 (with amino acid sequence PSRDECLTKNQ (SEQ ID NO: 52)), Heavy Chain Position 355 (with amino acid sequence SRDELCTKNQV (SEQ ID NO: 53)), Heavy Chain Position 357 (with amino acid sequence DELTKCNQVSL (SEQ ID NO: 54)), Heavy Chain Position 378 (with amino acid sequence IAVEWCESNGQ (SEQ ID NO: 55)), Heavy Chain Position 379 (with amino acid sequence AVEWECSNGOP (SEQ ID NO: 56)), Heavy Chain Position 386 (with amino acid sequence GQPENCNYKTT (SEQ ID NO: 57)), Heavy Chain Position 387 (with amino acid sequence QPENNCYKTTP (SEQ ID NO: 58)), and heavy chain position 410 (with amino acid sequence KLTVDCKSRWQ (SEQ ID NO: 59)). Antibodies that contain one or more of the cysteine insertion mutations described above maintain the ability of parental their antibody to bind to corresponding antigens (affinity). By performing antibody-toxin conjugate (TDCs) fixed-point coupling between a cysteine sulfhydryl group subject to light-chain insertion and/or a cysteine sulfhydryl group subject to heavy-chain insertion, a toxin to antibody ratio (DAR) of 1.6 to 2.0 or 3.2 to 4.0 can be realized.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing and other features of this disclosure will become more fully apparent from the following description and appended claims, taken in conjunction with the accompanying drawings. Understanding that these drawings depict only several embodiments arranged in accordance with the disclosure and are, therefore, not to be considered limiting of its scope, the disclosure will be described with additional specificity and detail through use of the accompanying drawings, in which:

EXAMPLES

Example 1: Synthesis of mc

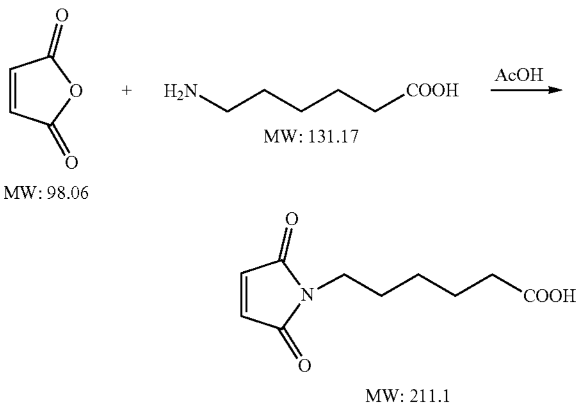

Figure 1:
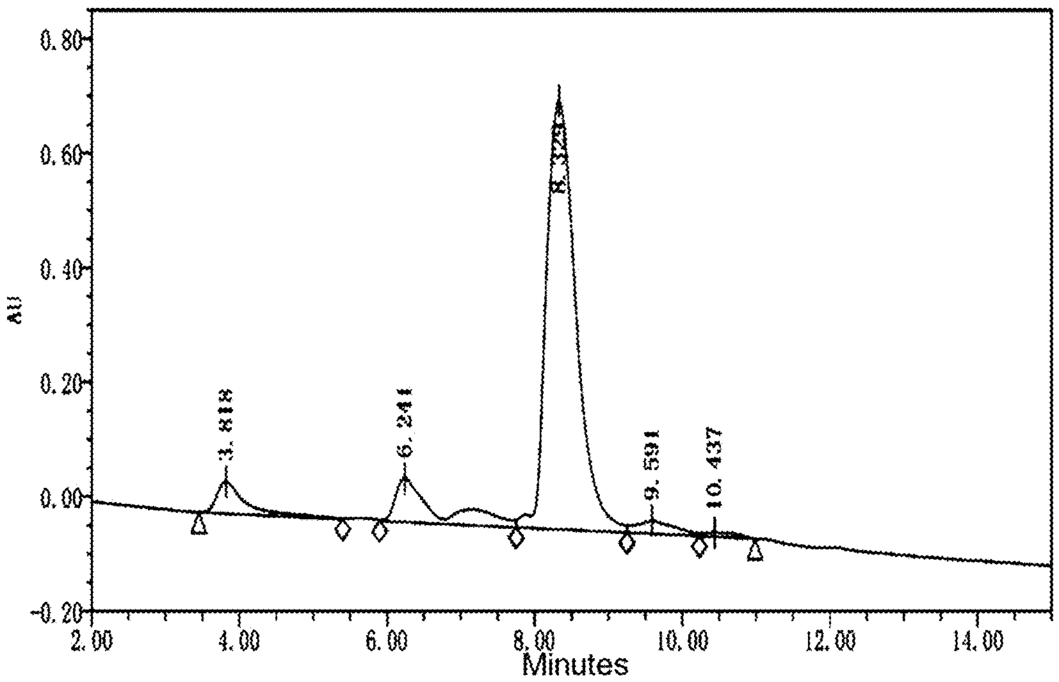
FIG. 1 demonstrates the HIC-HPLC measurement of toxin to antibody ratio (DAR) for 2A1-HC-Cys357ins-mc-vc-PAB-MMAE.

3.9 g (0.03 mol) of 6-aminocaproic acid and 3.5 g (0.036 mol) of 1.2 eq maleic anhydride were added to 30 ml of glacial acetic acid. The reaction solution was stirred at 120° C. for 4 to 6 hours. After the reaction was complete, heating was stopped and the solution was allowed to cool to room temperature naturally. The solution was then concentrated under reduced pressure at 60° C. to remove most of the acetic acid. The brownish yellow viscous liquid thus obtained was poured into water, ethyl acetate extraction was performed at 20 ml x 3 and the organic layers were combined. The organic layer was washed with water and saturated salt water in succession, dried with anhydrous sodium sulfate and filtered, and the filtrate was concentrated under reduced pressure to obtain a brownish yellow oily substance, after which 50 ml of water was added and stirring was performed, resulting in the precipitation of an off-white solid, which was filtered and dried at 50° C. under reduced pressure to obtain 5.08 g of target product, with a yield of 80%. mp: 89 to 92° C. m/z: 212.2 [M+H]+. 1HNMR (400 Mz, DMSO): 13.21 (br, 1H, COOH), 6.75 (s, 2H, COCH═CHCO), 3.63 (t, 2H, J=7.2 Hz, NCH2CH2), 2.42 (t, 2H, J=7.4 Hz, CH2COOH), 1.52-1.68 (m, 4H, NCH2CH2CH2CH2), 1.30-1.42 (m, 2H, NCH2CH2CH2CH2).

Example 2: Synthesis of Mc-OSu

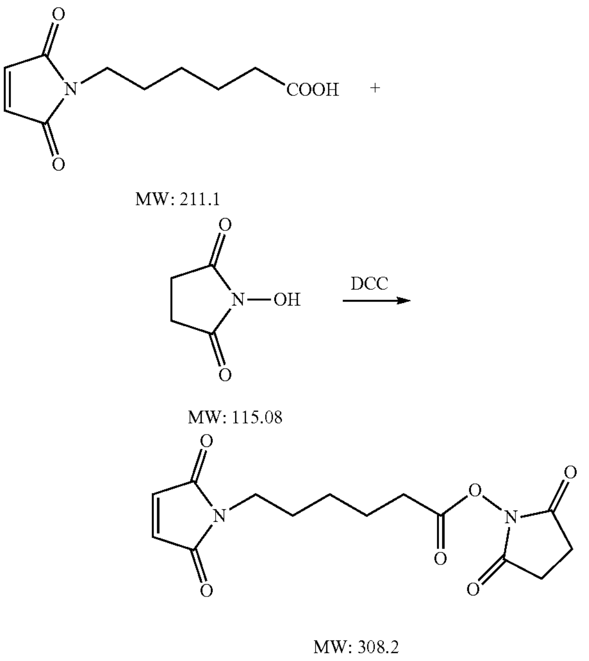

4.7 g (22 mmol) MC and 25 g (22 mmol) HOSu were added to 50 ml of acetonitrile under nitrogen gas. 4.5 g (22 mmol) of DCC was separately dissolved in 25 ml of acetonitrile while keeping the internal temperature at approximately 0° C., and the solution was slowly added dropwise to the above reaction solution. The reaction solution was allowed to react at 0° C. for two hours and then brought to room temperature before the reaction was allowed to continue overnight. Following filtration, the resulting filter cake was washed with acetonitrile at 10 ml x 3, and the filtrate was concentrated under reduced pressure until dry. The oil thus obtained was dried under reduced pressure at room temperature for six hours to obtain 6.4 g of a light brown solid, with a yield of 958. (It was then fed directly to the next reaction without further purification) m/z: 309.2 [M+H]+. 1HNMR (400Mz, CDCl3): 1-2 (m, 6H, CCH2CH2CH2C), 2.68 (t, 2H, CH2CO), 2.95 (s, 4H, COCH2CH2CO), 3.68 (t, 2H, CH2N), 6.81 (s, 2H), CH═CH).

Example 3: Synthesis of Fmoc-Val-OSu

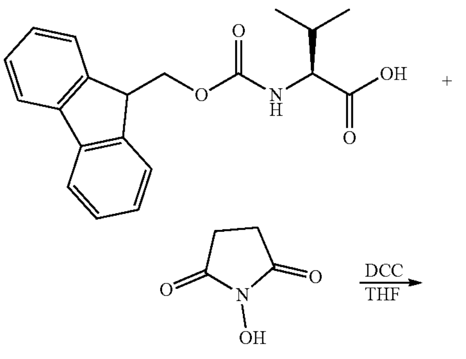

-continued

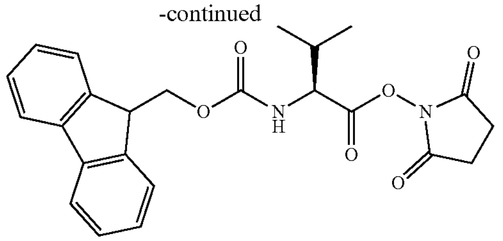

10 g of Fmoc-Val and 3.4 g of HOSu were added to 100 ml THF. 6 g of DCC was separately dissolved in 50 ml of acetonitrile while keeping the internal temperature at approximately 0° C., and the solution was slowly added dropwise to the above reaction solution. The reaction solution was stirred at room temperature for 24 hours. After filtration, the filter cake was washed with THE, and the filtrate was concentrated under reduced pressure to obtain a transparent oil. The oily substance was fed directly into the next reaction without further purification. m/z: 437.4 [M+H]+.

Example 4: Synthesis of Fmoc-vc

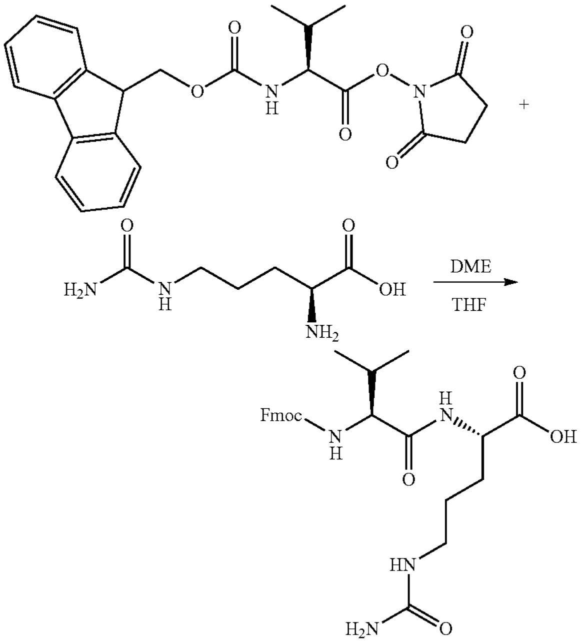

4.0 g (1.05 eq) of Cit and 60 ml of aqueous sodium bicarbonate solution ($NaHCO_3$, 2 g, 1.05 eq) were added to 20 ml of THE. 22.35 mmol of Fmoc-Val-OSu was separately dissolved in 60 ml DME, and the resulting solution was added to the reaction solution. The reaction solution was stirred at room temperature for 24 hours. After the reaction was completed, 110 ml of 15% citric acid aqueous solution was added to the system, and extraction was performed twice with EA and the organic layers were combined and concentrated under reduced pressure to obtain a white solid. 100 ml of methyl tert-butyl ether was added to the white solid and stirring was performed, followed by filtration; the filter cake was subject to drying under reduced pressure at 40° C. for 4h to obtain 4.83 g of product, with a yield of 65%. m/z: 497.6 (M+H)+. 1HNMR (400 Mz, DMSO): 0.92 (6H, m), 1.35-1.65 (4H, m), 2.10 (1H, m), 3.01 (2H, q), 3.99 (1H, t), 4.01-4.45 (2H, m), 4.45 (2H, t), 5.46 (2H, br), 6.03 (1H, t), 7.20-8.02 (8H, m), 8.25 (1H, d).

Example 5: Synthesis of Fmoc-vc-PABOH

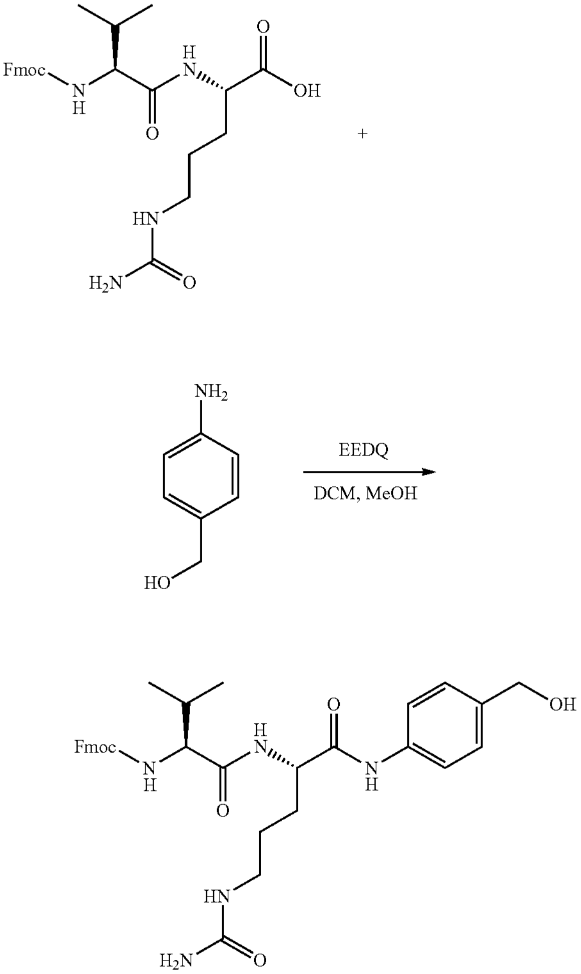

60 ml of DCM/MeOH=2/1 mixed solvent was added to a reaction flask, followed by addition of 2 g (4.2 mmol) Fmoc-vc and 1.04 g (2 eq) PABOH, after which the mixture was stirred to partial dissolution and 2.0 g (2 eq) EEDQ was added. The reaction system was allowed to continue reacting under stirring for 2.0 days in the dark at room temperature. After the reaction was completed, the reaction solution was concentrated under reduced pressure at 40° C. to obtain a white solid. The white solid was collected, 100 ml of methyl tert-butyl ether was added and stirring was performed, followed by filtration; the filter cake was washed with methyl tert-butyl ether, and the resulting white solid was dried under reduced pressure at 40° C., to obtain 2.2 g of product, with a yield of approximately 88%. m/z: 602.6 (M+H)+. 1HNMR (400 Mz, DMSO): 0.95 (6H, m), 1.45-1.69 (4H, m), 2.10 (1H, m), 3.11 (2H, m), 3.99 (1H, m), 4.30 (2H, d), 4.05-4.66 (2H, m), 4.55 (2H, d), 5.21 (1H, t), 5.51 (2H, br), 6.11 (1H, t), 7.09-8.10 (12H, m), 8.21 (1H, d), 10.51 (1H, br).

Example 6: Synthesis of vc-PABOH

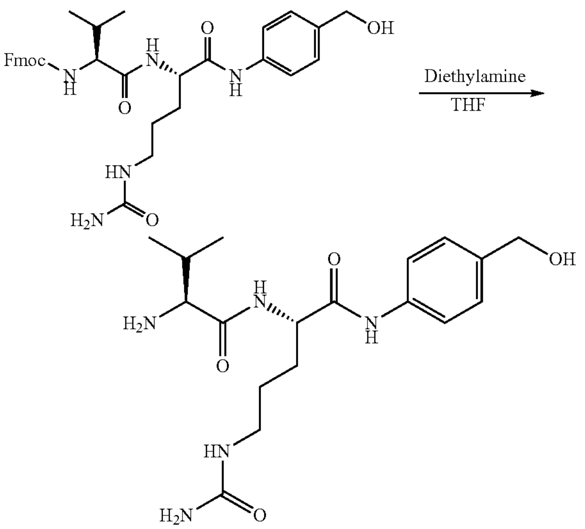

490 mg (0.815 mmol) of Fmoc-vc-PABOH was added to 10 ml of NMP and the mixture was stirred to dissolution, after which 2 ml of diethylamine was added. The reaction was then allowed to proceed under stirring at room temperature for 24 hours. After the reaction was complete, the solution was concentrated under reduced pressure at 40° C., 20 ml of DCM was added to the oily substance thus obtained and stirring was performed to obtain crystals which were filtered; the filter cake was then washed with DCM, and the solid thus obtained was dried under reduced pressure to obtain 277 mg of product, with a yield of 90%. m/z: 380.2 (M+H)+. 1HNMR (400 Mz, DMSO): 0.89 (6H, m), 1.31-1.61 (4H, m), 1.82 (1H, m), 2.86 (1H, m), 2.89 (2H, d), 4.38 (2H, d), 4.44 (1H, m), 5.01 (1H, br), 5.35 (2H, br), 5.84 (1H, br), 7.14 (2H, d), 7.42 (2H, d), 8.08 (1H, br), 9.88 (1H, br).

Example 7: Synthesis of mc-vc-PABOH

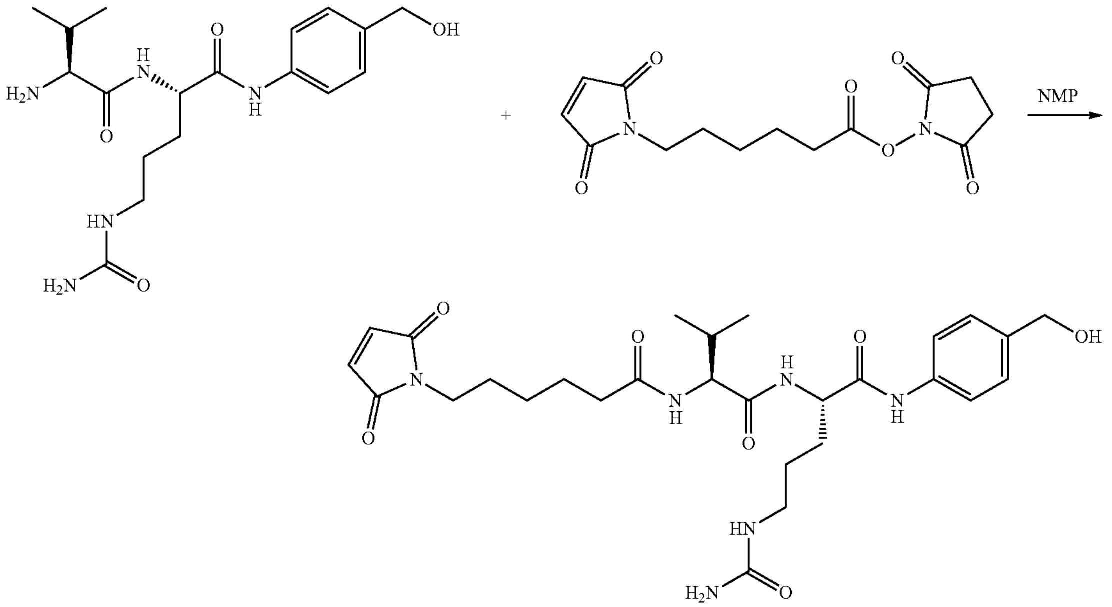

205 mg (0.54 mmol) of vc-PABOH and 184 mg (1.1 eq) of MC-OSu were added to 10 ml of NMP, and once addition was complete the reaction was allowed to proceed under stirring at room temperature for 24 hours. After the reaction was completed, the reaction solution was concentrated under reduced pressure at 40° C., 20 ml of methyl tert-butyl ether was added to the oily substance thus obtained and stirring was performed to obtain crystals. The crystals were then filtered and the filter cake was washed with methyl tert-butyl ether to obtain 310 mg of product, with a yield of 100%. m/z: 573.3 (M+H)+. 1HNMR (400 Mz, DMSO): 0.89 (6H, m), 1.15-1.99 (10H, m), 2.11 (1H, m), 2.31 (2H, t), 3.21 (2H, m), 3.53 (2H, t), 4.32 (1H, t), 4.51 (1H, m), 4.59 (2H, br), 5.24 (1H, br), 5.56 (2H, br), 6.20 (1H, br), 7.12 (2H, s), 7.23 (2H, d), 7.58 (2H, d), 7.94 (1H, d), 8.17 (1H, d), 10.21 (1H, br).

Example 8: Synthesis of mc-vc-PAB-PNP

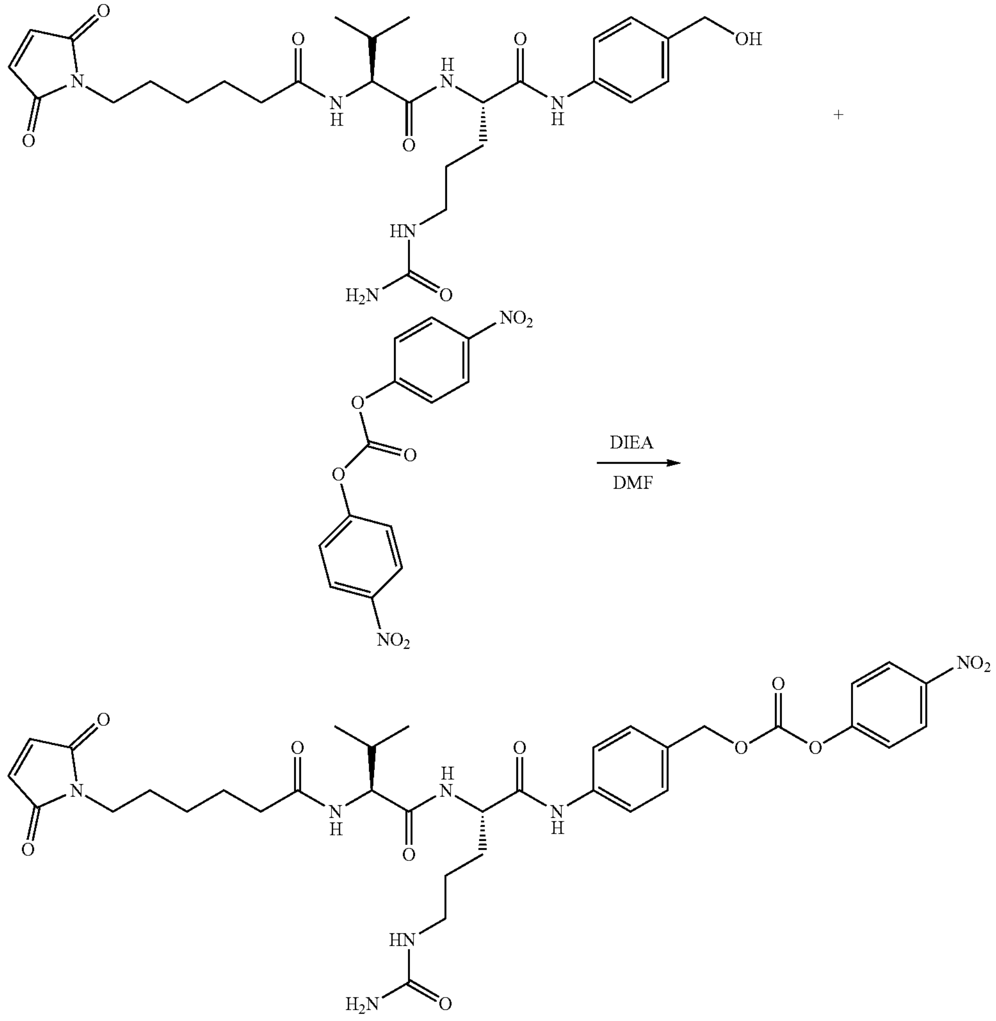

168.6 mg (0.294 mmol) of mc-vc-PABOH was dissolved in 5 ml of anhydrous pyridine under nitrogen gas, and the reaction system was cooled to approximately 0° C. 179 mg (3 eq) of PNP was separately dissolved in 5 ml of DCM, and the resulting solution was slowly added into the reaction system. After maintaining the temperature at 0° C. for 10 min, the ice bath was removed, and the reaction solution was stirred at room temperature for three hours. After the reaction was completed, 70 ml of EA and 100 ml of 15% citric acid aqueous solution were added, and the organic layer was separated off. The organic layer was washed with citric acid, water, and saturated brine in succession then dried over anhydrous sodium sulfate and filtered, and the filtrate was concentrated under reduced pressure until dry to obtain a light-yellow oil, after which methyl tert-butyl ether was added to induce crystallization and 86 mg of an off-white solid, with a yield of 40%. m/z: 738 (M+H)+. 1 HNMR (400 Mz, CDC13/CD3OD): 0.84 (6H, m), 1.11-1.84 (10H, m), 2.05 (1H, m), 2.15 (2H, t), 3.09 (2H, m), 3.32 (2H, t), 4.12 (1H, m), 4.38 (1H, m), 5.15 (2H, s), 6.61 (2H, s), 6.84 (1H, d), 7.61 (1H, d), 7.21 (2H, d), 7.50 (2H, d), 7.61 (2H, d), 8.18 (2H, d), 9.59 (1H, br).

Example 9: Synthesis of mc-vc-PAB-MMAE

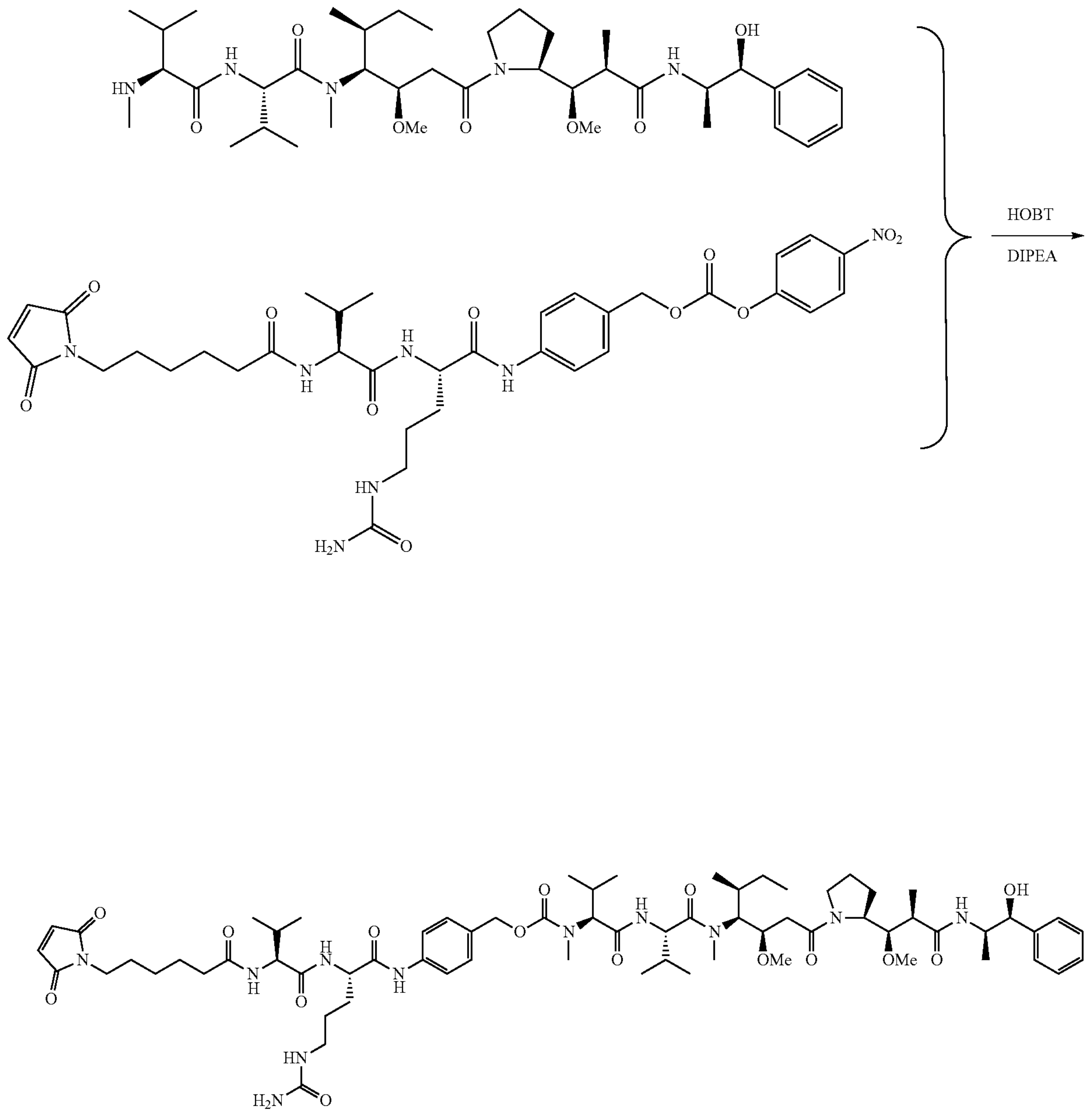

20 mg of mc-vc-PAB-PNP (1.5 eq) and 3 mg of HOBT were added to 2 ml of DMF. After briefly stirring the mixture at room temperature, 13 mg MMAE, 0.5 ml pyridine, and 25 ul DIEA were added. The reaction solution was stirred at room temperature for 2 days. After the reaction was complete, the reaction solution was directly purified using a preparative column, and the required components were collected, concentrated and lyophilized to obtain approximately 10 mg of product, with a yield of approximately 42%. m/z: 1317.1 (M+H)+.

Example 10: Synthesis of mc-vc-PAB-MMAF
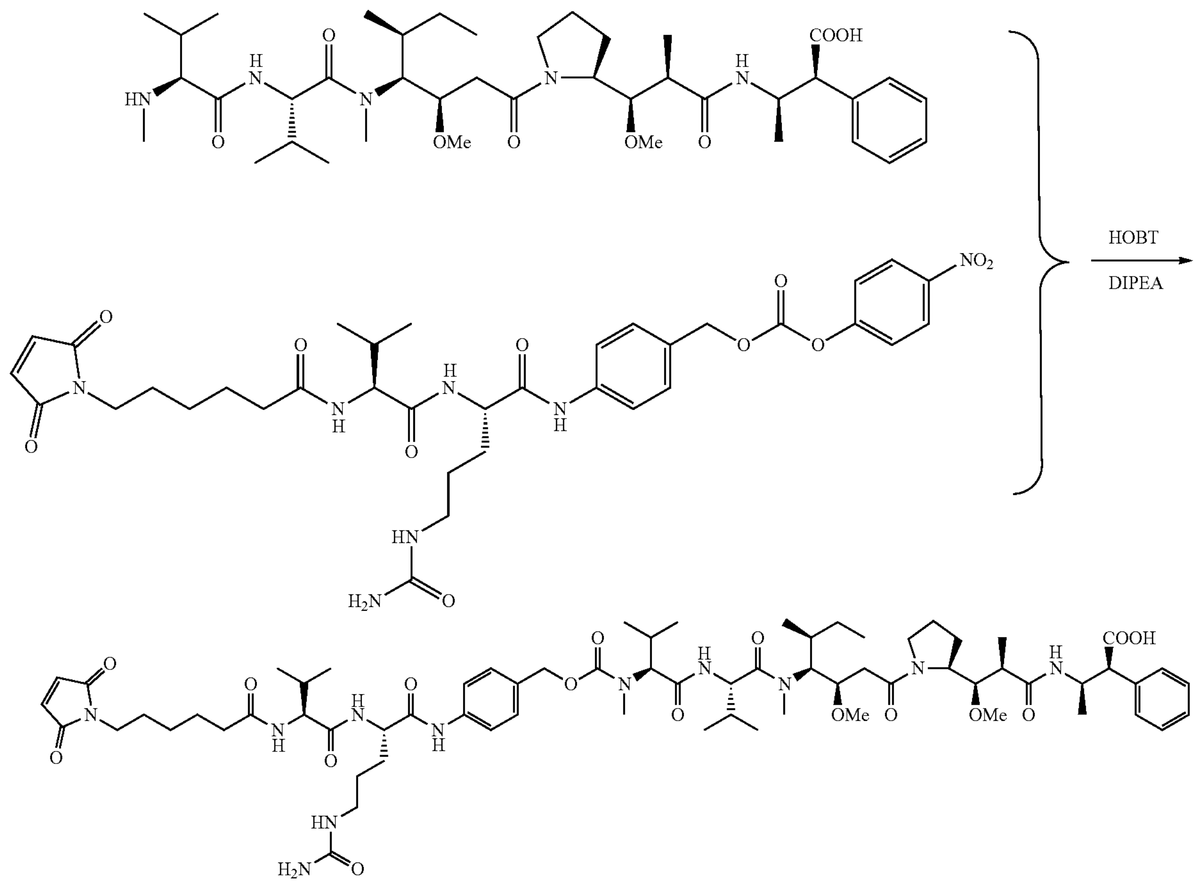
Using the same procedure as Example 9, approximately 12.5 mg of mc-vc-PAB-MMAF was obtained, with a yield of 45.2%; m/z: 1345.7 (M+H)+
Example 11 Synthesis of mc-vc-PAB-PBD
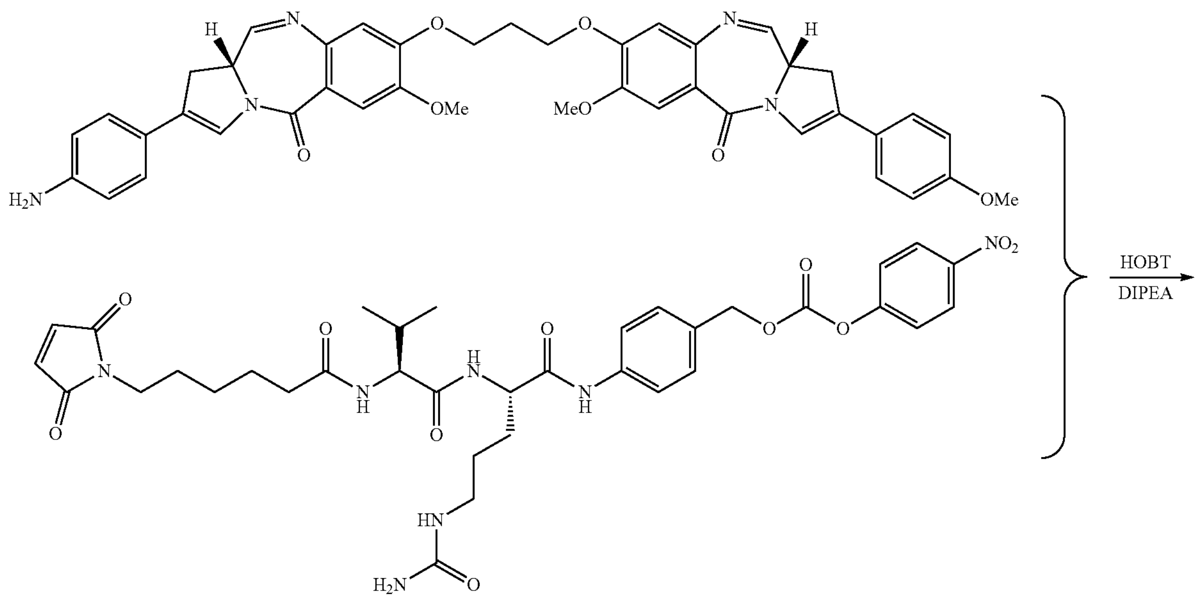

-continued
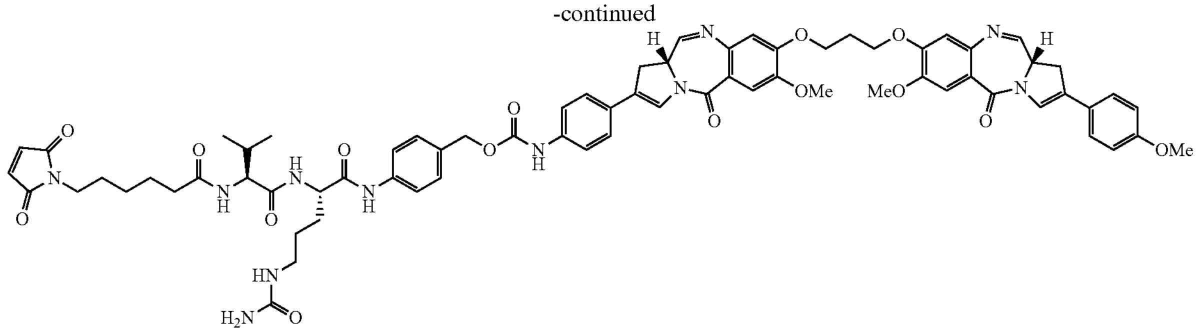
Using the same procedure as Example 9, approximately 9.5 mg of mc-vc-PAB-PBD was obtained, with a yield of 32.5%; m/z: 1325.4 (M+H)+
Example 12 Synthesis of mc-vc-PAB-DOX
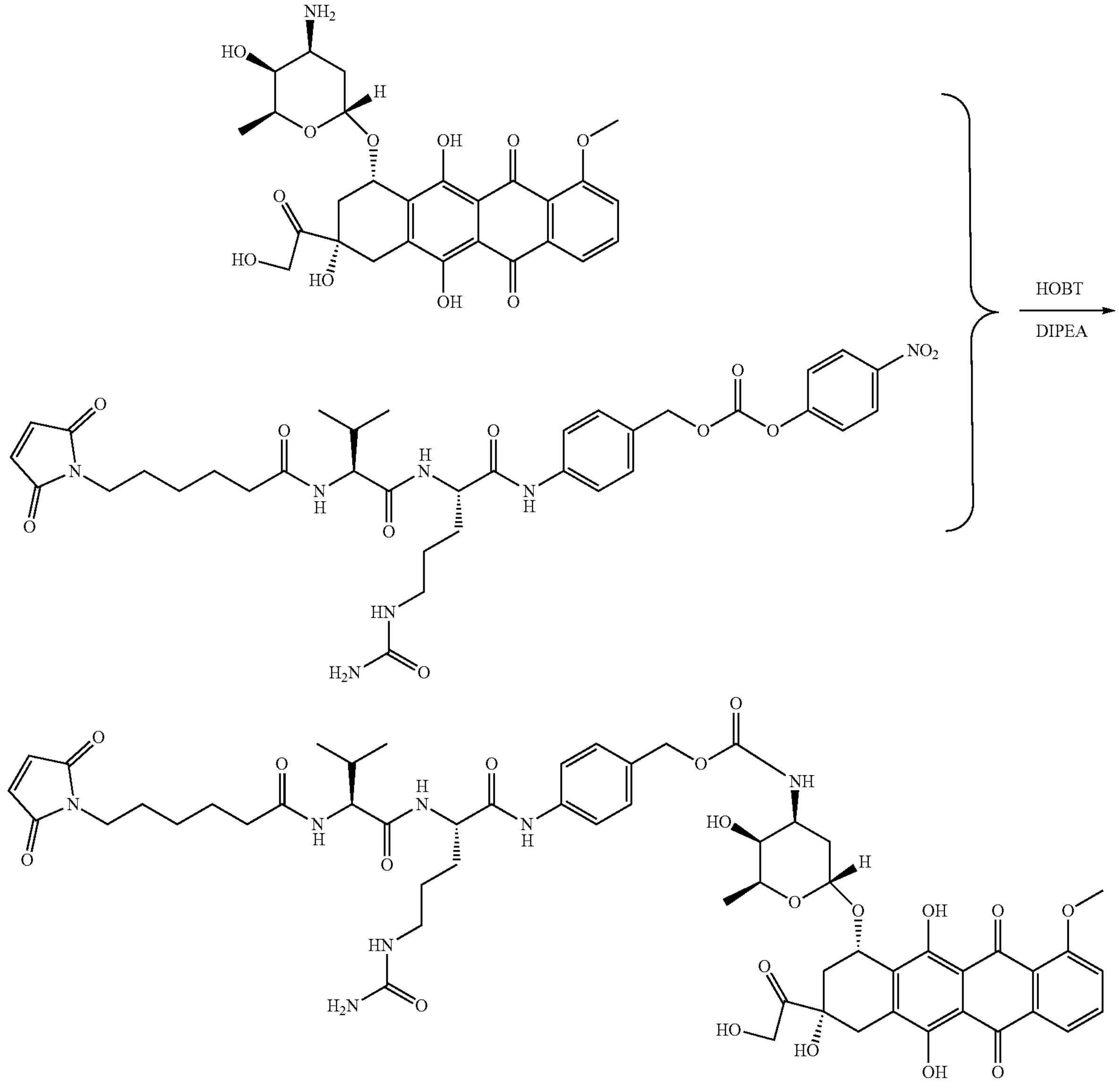

Using the same procedure as Example 9, approximately 11.2 mg of mc-vc-PAB-DOX was obtained, with a yield of 38.9%; m/z: 1143.2 (M+H)+

Example 13: Synthesis of mc-vc-PAB-SN-38

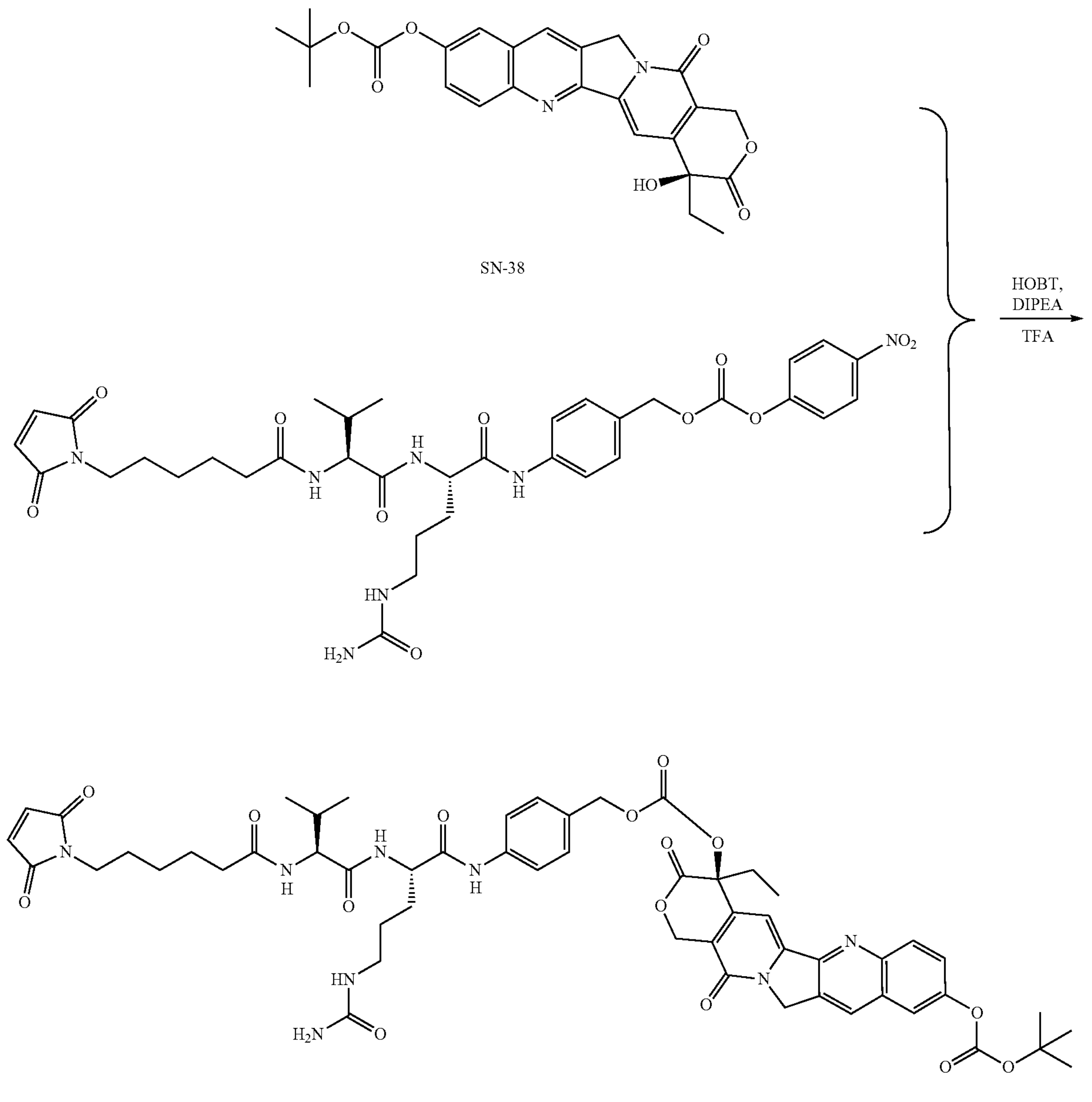

After dissolving 100 mg of commercially procured 10-O-Boc-SN-38 in 10 ml of dry dichloromethane, 25.6 mg (1 eq) DMAP was added, and a dichloromethane solution of triphosgene (62 mg triphosgene dissolved in 2 ml dichloromethane) was added dropwise at 0° C., after which the reaction was allowed to proceed at 0° C. for 12h; the dichloromethane was then removed under reduced pressure and the resulting substance was dissolved with 10 ml dry DMF, after which 144 mg of mc-vc-PABOH was added and the resulting mixture was stirred for 24 hours at room temperature and liquid phase isolation was carried out to obtain 41 mg of mc-vc-PAB-SN-38, with a total two-step yield of 19.7%, m/z: 1063.2 (M+H)+

Example 14: Expression and Purification of 2A1-HC-Cys254ins Antibody

Freestyle™ 293-F (Invitrogen) suspension cells were used to express the 2A1-HC-Cys254ins antibody. One day prior to transfection, cells were seeded at a density of $6\times10^5$ cells/mL in a 1 L shaker flask containing 300 mL of F17 complete medium (Freestyle™ F17 expression medium, Gibco) and incubated overnight at 37° C. and 5% CO-on a 120 cell rpm culture shaker. The following day, transfection of the antibody expression plasmid was carried out using PEI, where the ratio of plasmid to PEI was 2:1. One day after transfection, TN1 feed medium was added at 2.5% (v/v), the culture was run for a further four days and the supernatant was collected by centrifugation.

The resulting cell expression supernatant was collected and eluted with 0.1 M citric acid (pH 3.0) through a Protein A affinity chromatography column (Mabselect Sure LX, GE), and the captured antibodies were adjusted to pH 7.0 with 1 M Tris-HCl (pH 9.0) at 1/10 (v/v) and then passed through an SEC gel filtration chromatography column (Superdex 200, GE) to remove impurities such as polysomes and endotoxins, while the antibody buffer was replaced with PBS (pH 7.4) and UV280 nm target peak samples were collected and concentrated to 2 mg/ml using ultra-filtration centrifuge tubes (30KD, Pall). 2A1-HC-Cys254ins antibodies thus obtained showed a concentration of 2 mg/ml with a target antibody monomer ratio (POI %) greater than 90%, and were used in subsequent experiments.

Example 15: Preparation of 2A1-HC-Cys357ins-mc-vc-PAB-MMAE TDC Samples via Coupling of 2A1-HC-Cys357ins Antibody and mc-vc-PAB-MMAE Cell-expressed 2A1-HC-Cys357ins antibodies (SEQ ID NO: 34) were purified using Mabselect Sure and after elution at low pH, a Tris solution was immediately added to achieve neutralization, and the solution was exchanged to a Tris-HCl buffer of pH 7.5. The compound mc-vc-PAB-MMAE was a white powder and was dissolved in DMA for later use. The antibody needed to be first reduced to remove the barrier present on the mutant cysteine residue. 1M DTT aqueous solution was added at a 40× molecular ratio to the 2A1-HC-Cys357ins antibody solution and the resulting mixture was mixed well and allowed to react at 20° C. for two hours. Thereafter, the pH of the sample was adjusted to 5.0, and the DTT and barrier in the sample was removed via SP Sepharose FF cation exchange chromatography. Next, DHAA solution was added to the sample at a molecular ratio of 20× and the reaction was allowed to proceed for four hours at 25° C. in the dark to reconnect the disulfide bonds between the antibody chains. Thereafter, mc-vc-PAB-MMAE solution was added to induce coupling between mc-vc-PAB-MMAE and the antibody mutant cysteine, after which thorough mixing was performed and the reaction was allowed to proceed at 25° C. for two hours. After the reaction was complete, SP Sepharose FF cation exchange chromatography was used to remove the mc-vc-PAB-MMAE that was not coupled to an antibody molecule, and 2A1-HC-Cys357ins-mc-vc-PAB-MMAE TDC samples were obtained.

Example 16: HIC-HPLC Measurement of Toxin to Antibody Ratio (DAR)

TDC samples were analyzed via high performance liquid chromatography hydrophobic chromatography, and DAR was calculated based on corresponding peak area. The specific method used was as follows:

Column: Proteomix®HICBu-NP5 (5 μm, 4.6×35 mm);

Mobile Phases: A: 2M ammonium sulfate, 0.025M, pH 7 phosphate buffer; B: 0.025M, pH 7 phosphate buffer; C: 100% isopropanol;

Buffer A was equilibrated, Buffer B and Buffer C were used to perform a gradient elution and detection was carried out at 25° C. and 214 nm.

Figure 2:
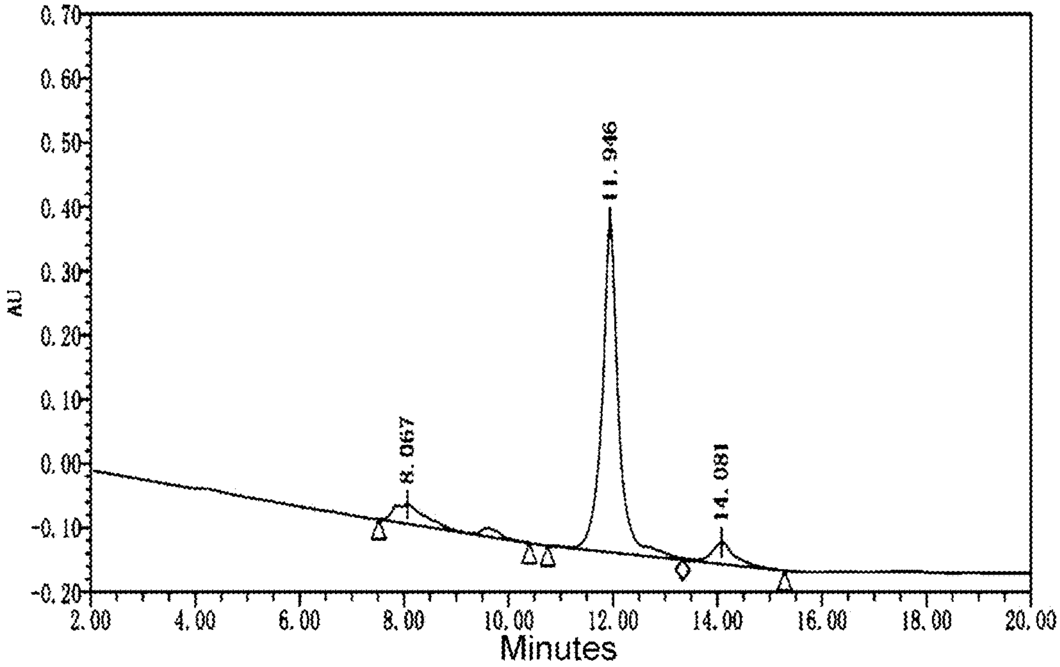
FIG. 2 demonstrates the HIC-HPLC measurement of toxin to antibody ratio (DAR) for 2A1-HC-Cys387ins-mc-vc-PAB-MMAE.
Figure 3:
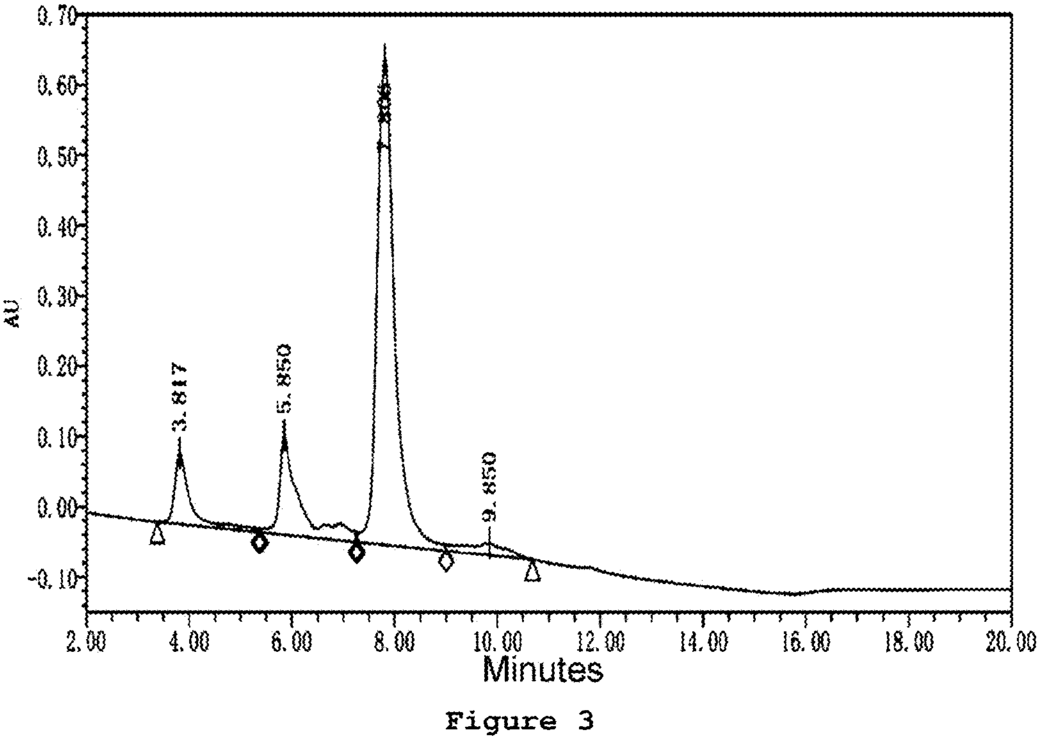
FIG. 3 demonstrates the HIC-HPLC measurement of toxin to antibody ratio (DAR) for 2A1-HC-Cys410ins-mc-vc-PAB-MMAE.
Figure 4:
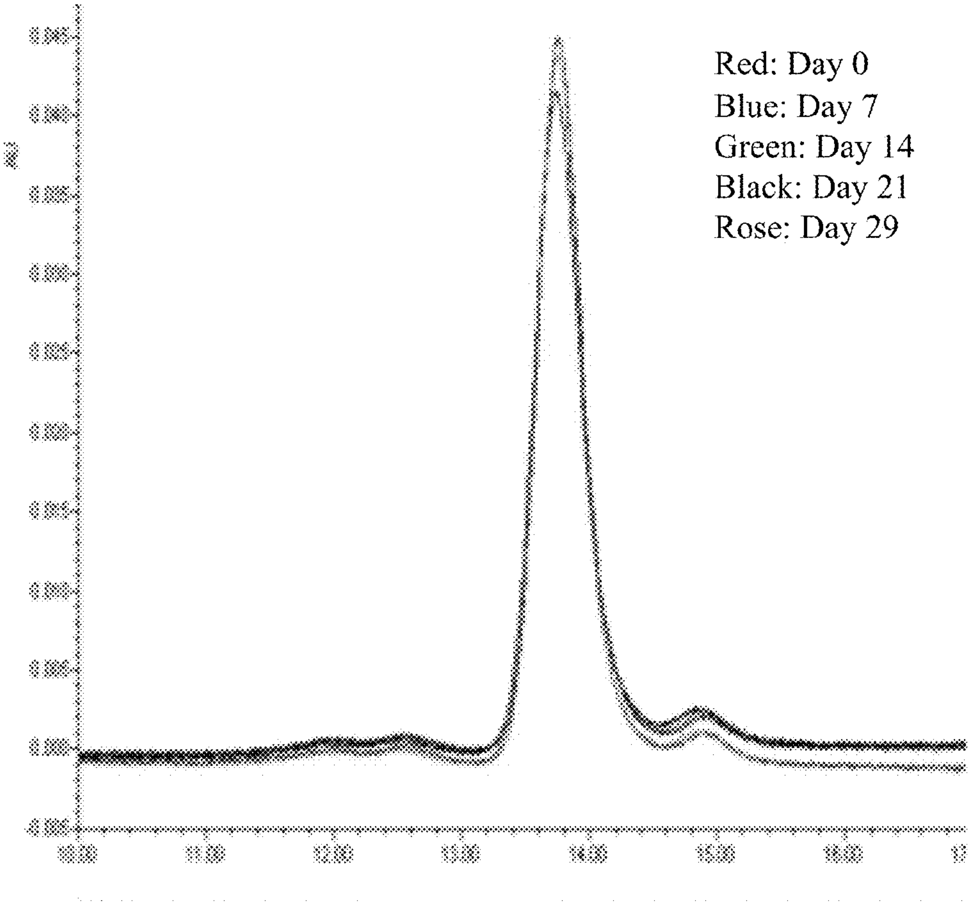
FIG. 4 shows SEC-HPLC detection of TDC antibody backbone stability and TDC aggregation of 2A1-HC-Cys357ins on Days 0, 7, 14, and 21.
Figure 5:
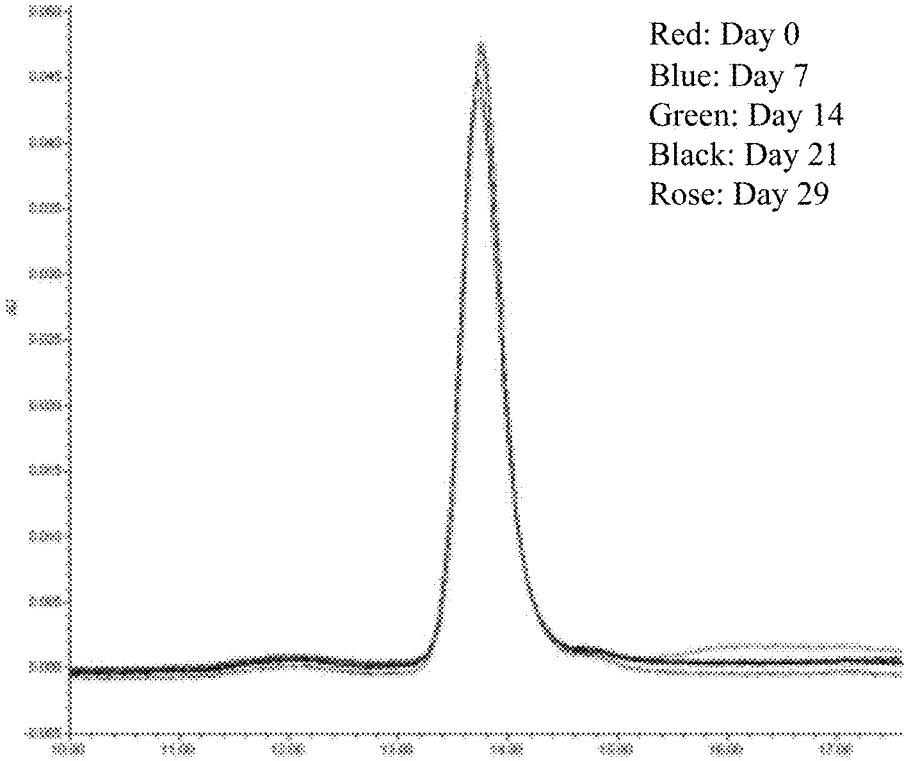
FIG. 5 shows SEC-HPLC detection of TDC antibody backbone stability and TDC aggregation of 2A1-HC-Cys387ins on Days 0, 7, 14, and 21.
Figure 6:
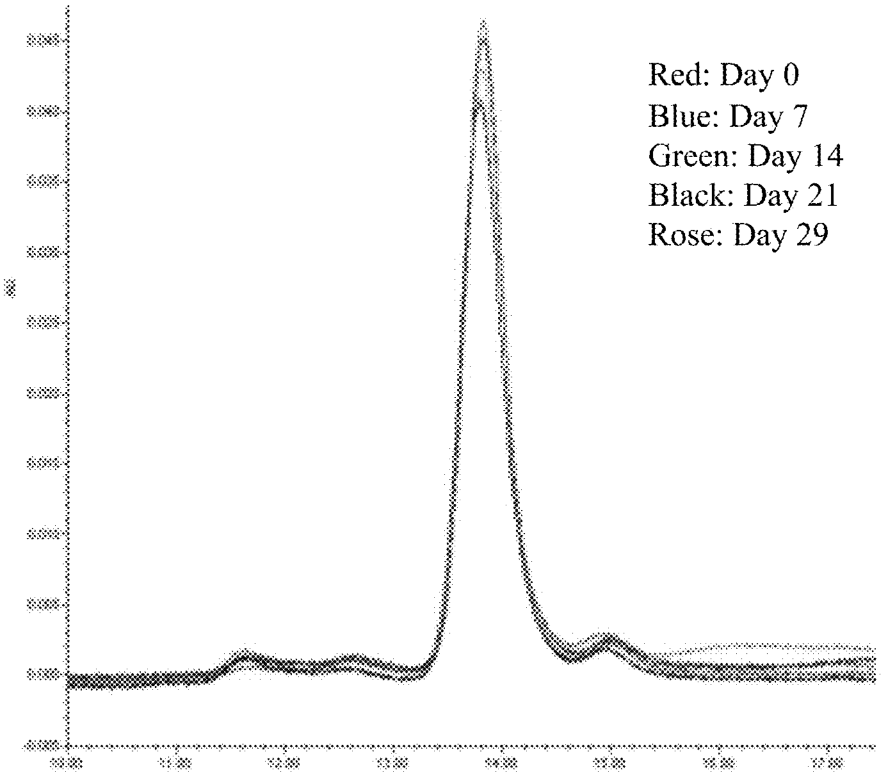
FIG. 6 shows SEC-HPLC detection of TDC antibody backbone stability and TDC aggregation of 2A1-HC-Cys378ins, on Days 0, 7, 14, and 21.
Figure 7:
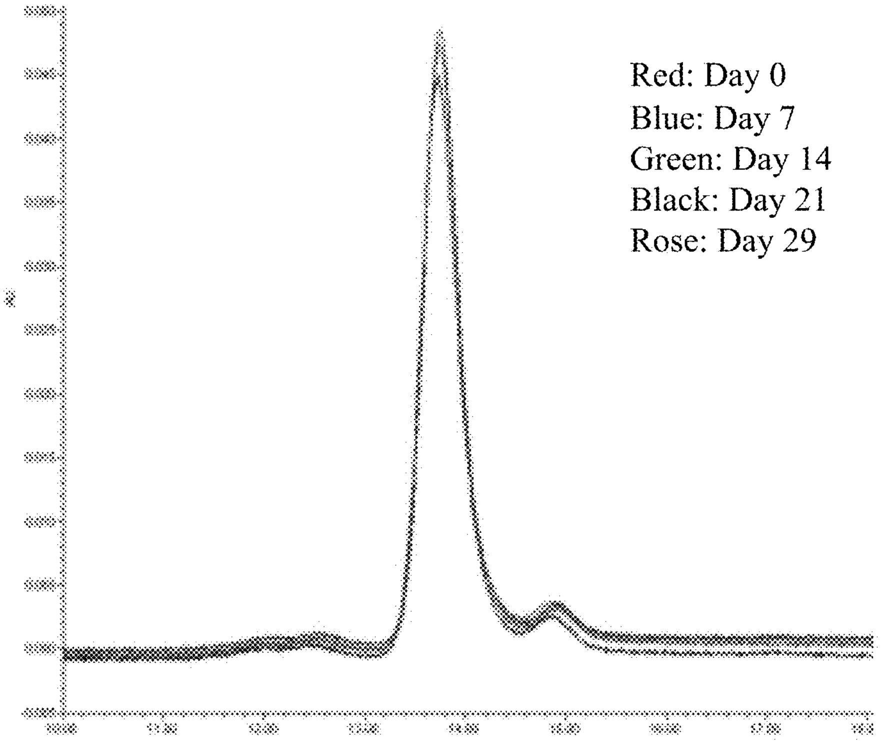
FIG. 7 shows SEC-HPLC detection of TDC antibody backbone stability and TDC aggregation of 2A1-HC-Cys410ins, on Days 0, 7, 14, and 21.
Figure 8:
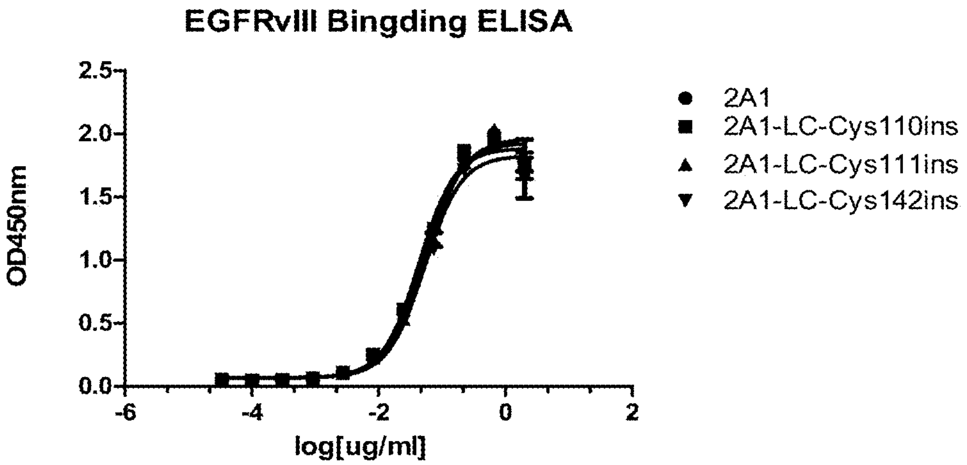
FIG. 8 shows the ELISA results comparing the relative affinities of 2A1-LC-Cys110ins-mc-vc-PAB-MMAE TDC, 2A1-LC-Cys111ins-mc-vc-PAB-MMAE TDC, 2A1-LC-Cys142ins-mc-vc-PAB-MMAE TDC, and 2A1 to EGFRvIII.
Figure 9:
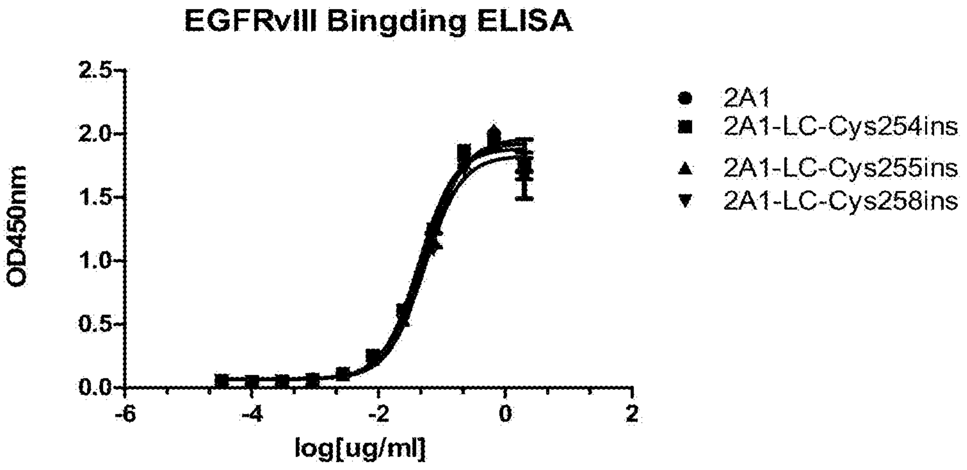
FIG. 9 shows the ELISA results comparing the relative affinities of 2A1-HC-Cys254ins-mc-vc-PAB-MMAE TDC, 2A1-HC-Cys255ins-mc-vc-PAB-MMAE TDC, 2A1-HC-Cys258ins-mc-vc-PAB-MMAE TDC, and 2A1 to EGFRvIII.
Figure 10:
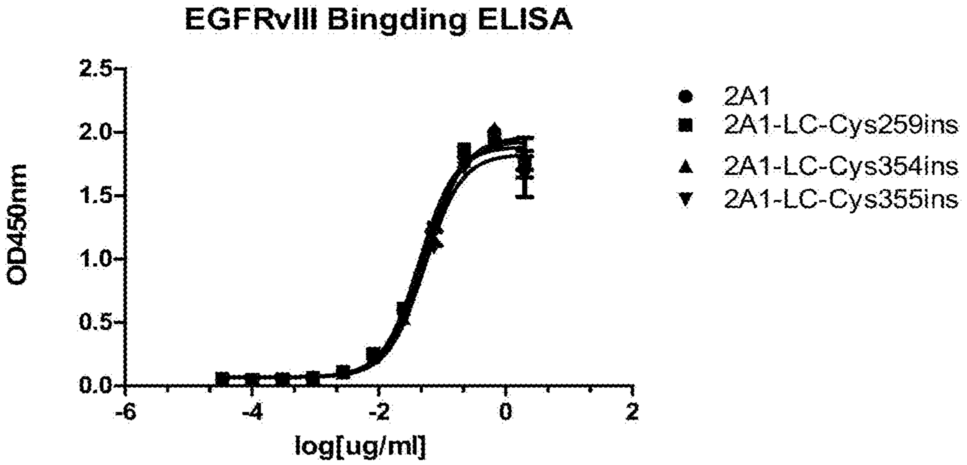
FIG. 10 shows the ELISA results comparing the relative affinities of 2A1-HC-Cys259ins-mc-vc-PAB-MMAE TDC, 2A1-HC-Cys354ins-mc-vc-PAB-MMAE TDC, 2A1-HC-Cys355ins-mc-vc-PAB-MMAE TDC, and 2A1 to EGFRvIII.
Figure 11:
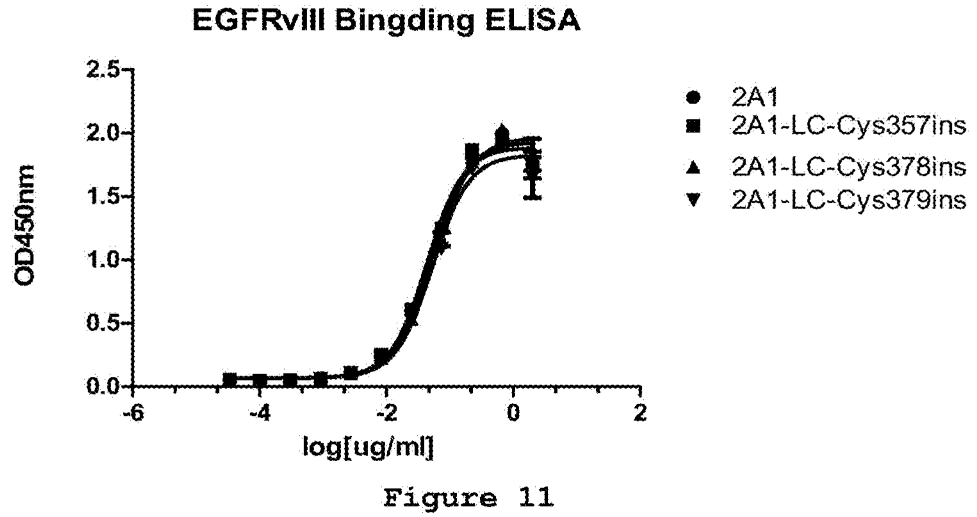
FIG. 11 shows the ELISA results comparing the relative affinities of 2A1-HC-Cys357ins-mc-vc-PAB-MMAE TDC, 2A1-HC-Cys378ins-mc-vc-PAB-MMAE TDC, 2A1-HC-Cys379ins-mc-vc-PAB-MMAE TDC, and 2A1 to EGFRvIII.
Figure 12:
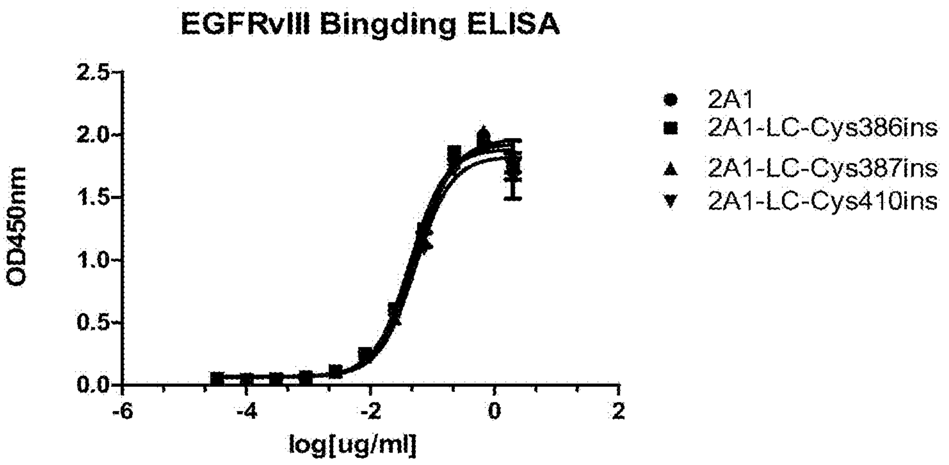
FIG. 12 shows the ELISA results comparing the relative affinities of 2A1-HC-Cys386ins-mc-vc-PAB-MMAE TDC, 2A1-HC-Cys387ins-mc-vc-PAB-MMAE TDC, 2A1-HC-Cys410ins-mc-vc-PAB-MMAE TDC, and 2A1 to EGFRvIII.

Appended FIGS. 1 through 3: HIC-HPLC detection of 2A1-HC-Cys357ins-mc-vc-PAB-MMAE, 2A1-HC-Cys378ins-mc-vc-PAB-MMAE, 2A1-HC-Cys387ins-mc-vc-PAB-MMAE and 2A1-HC-Cys410ins-mc-vc-PAB-MMAE TDC DAR, respectively.

The data in FIGS. 1 through 3 were used to calculate that the DARs of the fixed-point couplings ranged between 1.6 and 1.7, and the compound showed good uniformity.

Appended Table 1: 2A1-LC-Cys110ins-mc-vc-PAB-MMAE TDC, 2A1-LC-Cys111ins-mc-vc-PAB-MMAE TDC, 2A1-LC-Cys142ins-mc-vc-PAB-MMAE TDC, 2A1-HC-Cys254ins-mc-vc-PAB-MMAE TDC, 2A1-HC-Cys255ins-mc-vc-PAB-MMAE TDC, 2A1-HC-Cys258ins-mc-VC-PAB-MMAE TDC, 2A1-HC-Cys259ins-mc-vc-PAB-MMAE TDC, 2A1-HC-Cys354ins-mc-vc-PAB-MMAE TDC, 2A1-HC-Cys355ins-mc-vc-PAB-MMAE TDC, 2A1-HC-Cys357ins-mc-vc-PAB-MMAE TDC, 2A1-HC-Cys378ins-mc-vc-PAB-MMAE TDC, 2A1-HC-Cys379ins-mc-vc-PAB-MMAE TDC, 2A1-HC-Cys386ins-mc-vc-PAB-MMAE TDC, 2A1-HC-Cys387ins-mc-vc-PAB-MMAE TDC and 2A1-HC-Cys410ins-mc-vc-PAB-MMAE

APPENDED TABLE 1

Table showing TDC coupling efficiency (DAR)

| | Compound Name | DAR |
|---|---|---|
| Fixed-Point Coupling (TDC) | 2A1-LC-Cys110ins-mc-vc-PAB-MMAE TDC | 1.82 |
| | 2A1-LC-Cys111ins-mc-vc-PAB-MMAE TDC | 1.78 |
| | 2A1-LC-Cys142ins-mc-vc-PAB-MMAE TDC | 1.68 |
| | 2A1-HC-Cys254ins-mc-vc-PAB-MMAE TDC | 1.74 |
| | 2A1-HC-Cys255ins-mc-vc-PAB-MMAE TDC | 1.77 |
| | 2A1-HC-Cys258ins-mc-vc-PAB-MMAE TDC | 1.75 |
| | 2A1-HC-Cys259ins-mc-vc-PAB-MMAE TDC | 1.80 |
| | 2A1-HC-Cys354ins-mc-vc-PAB-MMAE TDC | 1.75 |
| | 2A1-HC-Cys355ins-mc-vc-PAB-MMAE TDC | 1.75 |
| | 2A1-HC-Cys357ins-mc-vc-PAB-MMAE TDC | 1.83 |
| | 2A1-HC-Cys378ins-mc-vc-PAB-MMAE TDC | 1.50 |
| | 2A1-HC-Cys379ins-mc-vc-PAB-MMAE TDC | 1.86 |
| | 2A1-HC-Cys386ins-mc-vc-PAB-MMAE TDC | 1.77 |
| | 2A1-HC-Cys387ins-mc-vc-PAB-MMAE TDC | 1.83 |
| | 2A1-HC-Cys410ins-mc-vc-PAB-MMAE TDC | 1.86 |

Appended Table 1 shows that the coupling efficiency of TDC compounds subject to fixed-point coupling via cysteine insertion mutation modification is relatively high (theoretical maximum value is 2.0), and DAR was ≥ 1.6.

Example 17: SEC-HPLC Detection of TDC Antibody Backbone Stability and TDC Aggregation TDC antibody backbone samples were stored at 37° C., and aggregation was analyzed by SEC-HPLC on Days 0, 7, 14 and 21. The specific methodology was as follows:

Column: TSKgel SuperSW mAb HR (7.8 mm×30 cm)

Mobile Phase: 0.1M sodium sulfate, 0.1M pH 6.7 phosphate buffer.

Detection was performed at 25° C. and 280 nm.

APPENDED TABLE 2

| | | POI % | | | |
|---|---|---|---|---|---|
| | Compound Name | 0 day | 7 day | 14 day | 29 day |
| Fixed-Point Coupling (TDC) | 2A1-HC-Cys357ins | 99.4 | 98.7 | 98.1 | 96.5 |
| | 2A1-HC-Cys387ins | 99.1 | 98.6 | 97.6 | 95.7 |
| | 2A1-HC-Cys410ins | 98.8 | 98.1 | 97.2 | 95.1 |
| | 2A1-HC-Cys378ins | 99.4 | 99.3 | 99.1 | 98.7 |

Appended FIGS. 4 through 7: 2A1-HC-Cys378ins SEC results on Days 0, 7, 14, and 21. The data show that the sample was high stable when stored at 37° C. for three weeks.

Appended Table 2: SEC-HPLC detection of aggregation of TDC antibody backbones 2A1-HC-Cys357ins, 2A1-HC-Cys387ins, 2A1-HC-Cys378ins, and 2A1-HC-Cys410ins; the samples were stored at 37° C. for three weeks with fundamentally no change in monomeric POI content;

2A1-LC-Cys110ins-mc-vc-PAB-MMAE TDC, 2A1-LC-Cys111ins-mc-vc-PAB-MMAE TDC, 2A1-LC-Cys142ins-mc-vc-PAB-MMAE TDC, 2A1-HC-Cys254ins-mc-vc-PAB-MMAE TDC, 2A1-HC-Cys255ins-mc-vc-PAB-MMAE TDC, 2A1-HC-Cys258ins-mc-vc-PAB-MMAE TDC, 2A1-HC-Cys259ins-mc-vc-PAB-MMAE TDC, 2A1-HC-Cys354ins-mc-vc-PAB-MMAE TDC, 2A1-HC-Cys355ins-mc-vc-PAB-MMAE TDC, 2A1-HC-Cys357ins-mc-vc-PAB-MMAE TDC, 2A1-HC-Cys378ins-mc-vc-PAB-MMAE TDC, 2A1-HC-Cys379ins-mc-vc-PAB-MMAE TDC, 2A1-HC-Cys386ins-mc-vc-PAB-MMAE TDC, 2A1-HC-Cys387ins-mc-vc-PAB-MMAE TDC and 2A1-HC-Cys410ins-mc-vc-PAB-MMAE

APPENDED TABLE 3

TDC target monomer content

| | Compound Name | POI % |
|---|---|---|
| Fixed-Point Coupling (TDC) | 2A1-LC-Cys110ins-mc-vc-PAB-MMAE TDC | 93.6% |
| | 2A1-LC-Cys111ins-mc-vc-PAB-MMAE TDC | 91.7% |
| | 2A1-LC-Cys112ins-mc-vc-PAB-MMAE TDC | 92.4% |
| | 2A1-HC-Cys254ins-mc-vc-PAB-MMAE TDC | 93.3% |
| | 2A1-HC-Cys255ins-mc-vc-PAB-MMAE TDC | 91.2% |
| | 2A1-HC-Cys258ins-mc-vc-PAB-MMAE TDC | 94.2% |
| | 2A1-HC-Cys259ins-mc-vc-PAB-MMAE TDC | 93.4% |
| | 2A1-HC-Cvs354ins-mc-vc-PAB-MMAE TDC | 94.7% |
| | 2A1-HC-Cys355ins-mc-vc-PAB-MMAE TDC | 96.72% |
| | 2A1-HC-Cys357ins-mc-vc-PAB-MMAE TDC | 91.47% |
| | 2A1-HC-Cys378ins-mc-vc-PAB-MMAE TDC | 75.06% |
| | 2A1-HC-Cys379ins-mc-vc-PAB-MMAE TDC | 93.42% |
| | 2A1-HC-Cys386ins-mc-vc-PAB-MMAE TDC | 97.49% |
| | 2A1-HC-Cys387ins-mc-vc-PAB-MMAE TDC | 96.61% |
| | 2A1-HC-Cys410ins-mc-vc-PAB-MMAE TDC | 97.74% |

Appended Table 3 shows that the target monomer content of TDC compounds subject to cysteine fixed-point coupling was greater than 90%.

Example 18: Affinity of Antibody Backbone after Cysteine

Insertion Mutation Modification and Parent Antibody 2A1 for EGFRvIII

ELISA was used to compare the relative affinities of 2A1-LC-Cys110ins-mc-vc-PAB-MMAE TDC, 2A1-LC-Cys111ins-mc-vc-PAB-MMAE TDC, 2A1-LC-Cys142ins-mc-vc-PAB-MMAE TDC, 2A1-HC-Cys254ins-mc-vc-PAB-MMAE TDC, 2A1-HC-Cys255ins-mc-vc-PAB-MMAE TDC, 2A1-HC-Cys258ins-mc-vc-PAB-MMAE TDC, 2A1-HC-Cys259ins-mc-vc-PAB-MMAE TDC, 2A1-HC-Cys354ins-mc-vc-PAB-MMAE TDC, 2A1-HC-Cys355ins-mc-vc-PAB-MMAE TDC, 2A1-HC-Cys357ins-mc-vc-PAB-MMAE TDC, 2A1-HC-Cys378ins-mc-vc-PAB-MMAE TDC, 2A1-HC-Cys379ins-mc-vc-PAB-MMAE TDC, 2A1-HC-Cys386ins-mc-vc-PAB-MMAE TDC, 2A1-HC-Cys387ins-mc-vc-PAB-MMAE TDC, 2A1-HC-Cys410ins-mc-vc-PAB-MMAE TDC, and 2A1 for EGFRvIII. The specific process used was as follows:

Recombinant EGFRVIII-His*6 antigen was used to coat plates; fish skin gelatin was used as a seal; dilution of each insertion mutant antibody was performed separately, up to a maximum concentration 10 μg/ml and a 4-fold gradient dilution was performed for a total of 11 concentrations; HRP-labeled secondary antibodies were used for incubation; TMB was used for development and absorption detection was performed at 450 nm. Assay results were plotted as A450 paired concentrations, and as shown in FIG. 3 and Table 3, the antibodies subject to cysteine insertion mutation maintained similar affinity for 2A1, with EC50 values very close to each other, indicating that light- or heavy-chain insertion mutations on 2A1 do not affect affinity for the antigen EGFRVIII.

APPENDED TABLE 4

Determination of mutant antibody affinity

| | Antibody Mutation | $R^2$ | EC50 (nM) |
|---|---|---|---|
| Antibody | 2A1-LC-Cys110ins | 0.9948 | 0.04039 |
| | 2A1-LC-Cys111ins | 0.9957 | 0.04667 |
| | 2A1-LC-Cys142ins | 0.9951 | 0.04976 |
| | 2A1-HC-Cys254ins | 0.9956 | 0.04556 |
| | 2A1-HC-Cys255ins | 0.9932 | 0.03904 |
| | 2A1-HC-Cys258ins | 0.9955 | 0.04231 |
| | 2A1-HC-Cys259ins | 0.9946 | 0.04308 |
| | 2A1-HC-Cys354ins | 0.9951 | 0.04053 |
| | 2A1-HC-Cys355ins | 0.9954 | 0.04152 |
| | 2A1-HC-Cys357ins | 0.9974 | 0.04031 |
| | 2A1-HC-Cys378ins | 0.9964 | 0.04039 |
| | 2A1-HC-Cys379ins | 0.9952 | 0.04089 |
| | 2A1-HC-Cys386ins | 0.9918 | 0.04346 |
| | 2A1-HC-Cys387ins | 0.9974 | 0.04516 |
| | 2A1-HC-Cys410ins | 0.9978 | 0.04204 |

Appended FIGS. 8 through 12 and Appended Table 4: 2A1-LC-Cys110ins (SEQ ID NO: 16), 2A1-LC-Cys111ins (SEQ ID NO: 18), 2A1-LC-Cys142ins (SEQ ID NO:20), 2A1-HC-Cys254ins (SEQ ID NO: 22), 2A1-HC-Cys255ins (SEQ ID NO: 24), 2A1-HC-Cys258ins (SEQ ID NO:26), 2A1-HC-Cys259ins (SEQ ID NO:28), 2A1-HC-Cys354ins (SEQ ID NO: 30), 2A1-HC-Cys355ins (SEQ ID NO:32), 2A1-HC-Cys357ins (SEQ ID NO: 34), 2A1-HC-Cys378ins (SEQ ID NO: 36), 2A1-HC-Cys379ins (SEQ ID NO:38), 2A1-HC-Cys386ins (SEQ ID NO: 40), 2A1-HC-Cys387ins (SEQ ID NO: 42) and 2A1-HC-Cys410ins (SEQ ID NO: 44) antibodies maintained 2A1 affinity for the antigen EGFRvIII.

Example 19: Cytotoxicity Testing

TDC cytotoxic activity was determined via the following experimental procedure: TDC was added to EGFR-overexpressing or EGFRVIII-expressing human tumor cell culture medium, and cell viability was determined after 72 hours of cell culture. Cell-based in vitro experiments were used to determine cell viability, cytotoxicity and programmed cell death induced by TDC constituted by the present invention.

In vitro efficacy of antibody-toxin conjugates was determined via a cell proliferation assay. A CellTiter $^{96}$® AqueousOne Solution Cell was Proliferation Assay purchased commercially from Promega Corp. (Madison, WI). CellTiter $^{96}$® Aqueous One Solution Cell Proliferation Assay (a) is a colorimetric method used to detect the number of living cells in cell proliferation and cytotoxicity experiments. The above reagent contains the novel tetrazole compound [3-(4,5-dimethylthiazol-2-yl)-5-(3-carboxymethoxyphenyl)-2-(4-sulfophenyl)-2H-tetrazolium, inner salt; MTS) as well as an electronic coupling agent (phenazine ethosulfate; PES). PES exhibits enhanced chemical stability, which allows it to be mixed with MTS to form a stable solution. This convenient "single solution" model is an improvement on the first generation of the CellTiter $^{96}$® Aqueous Assay, in which the electronic coupling agent PMS was supplied separately from the MTS solution. MTS (Owen's reagent) is reduced by cellular organisms into a colored formazan product, which can be directly dissolved in culture medium (FIG. 1). This conversion is likely facilitated by NADPH NADH produced by dehydrogenase present in metabolically active cells. For the assay, a small amount of CellTiter $^{96}$® Aqueous One Solution Reagent is added directly to the medium present in the wells of the culture plate, after which incubation is performed for 1 to 4 hours, followed by reading of the absorbance value at 490 nm using a microplate reader.

Figure 1. The structure of MTS tetrazolium salt and its formazan product

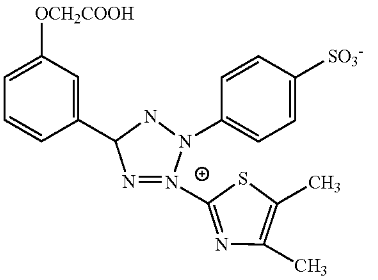

MTS

-continued

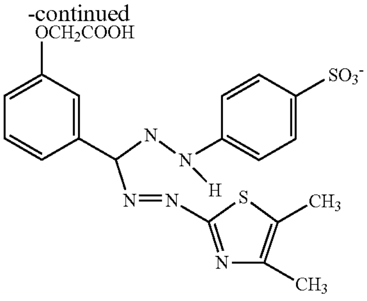

Formazan

The amount of formazan product detected at 490 nm is proportional to the number of viable cells in culture. Because the formazan product of MTS is soluble in tissue culture medium, CellTiter $^{96}$® Aqueous One Solution Assay requires fewer steps than the MTT or INT methods. A431 (EGFR-overexpressing cells) and U87-EGFRVIII (an EGFRVIII mutant stable cell line) were used in the present invention as an investigative system for performing in vitro efficacy assays. In 96-well plates, cells were plated at 6000 cells/well and 24 hours later, antibody spiking was carried out. The dosing concentrations for A431 and U87-EGFRVIII ranged from 200 nM to 10 pM with a four-fold dilution performed, and the concentration of U87-EGFRVIII ranged from 500 nM to 30 pM. Cell viability was assayed via MTS 72 hours after treatment.

Figure 13:
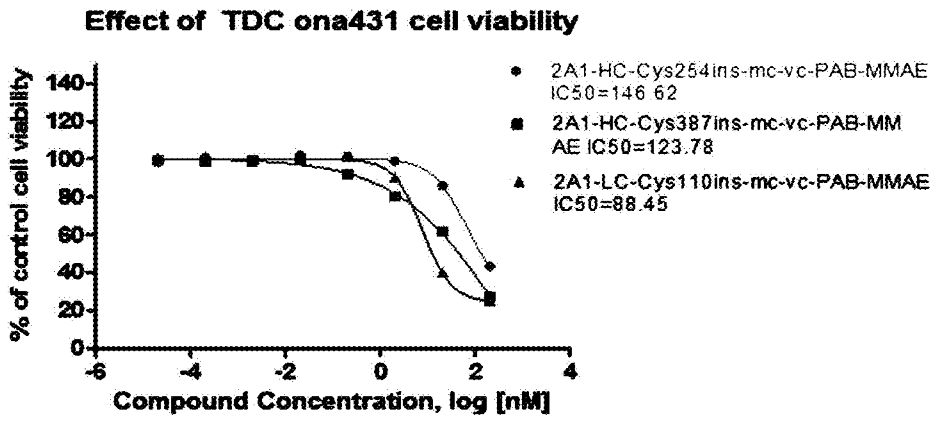
FIG. 13 depicts the effect of TDC on the cell viability of A431, a human skin squamous cell carcinoma cell line overexpressing EGFRwt, for measuring IC50 for 2A1-HC-Cys357ins-mc-vc-PAB-MMAE, 2A1-HC-Cys378ins-mc-vc-PAB-MMAE, and 2A1-HC-Cys387ins-mc-vc-PAB-MMAE.
Figure 14:
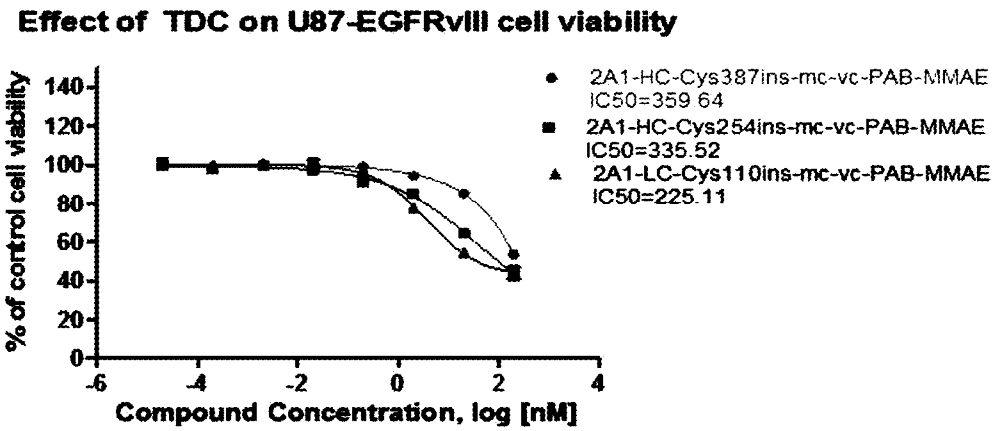
FIG. 14 depicts the effect of TDC on the cell viability of U87-EGFRvIII, a human glioma cell line overexpressing EFGRvIII, for measuring IC50 for 2A1-HC-Cys357ins-mcvc-PAB-MMAE, 2A1-HC-Cys378ins-mc-vc-PAB-MMAE, and 2A1-HC-Cys387ins-mc-vc-PAB-MMAE.

Appended FIGS. 13 and 14: IC50 test results for 2A1-HC-Cys357ins-mc-vc-PAB-MMAE, 2A1-HC-Cys378ins-mc-vc-PAB-MMAE, 2A1-HC-Cys387ins-mc-vc-PAB-MMAE and 2A1-HC-Cys410ins-mc-vc-PAB-MMAE on the EGFRwt-overexpressing human skin squamous cell carcinoma cell line A431 and the EFGRvIII-overexpressing human glioma cell line U87-EGFRvIII.

APPENDED TABLE 5

$IC_{50}$ test results showing TDC cytotoxicity for EGFRwt-overexpressing cell line A431 and the EFGRvIII-overexpressing cell line U87-EGFRvIII

| | | MTS | |
|---|---|---|---|
| | Compound | A431 | U87MG-EGFRvIII |
| Antibody | 2A1-LC-Cys110ins | >10 μM | >10 μM |
| | 2A1-LC-Cys111ins | >10 μM | >10 μM |
| | 2A1-LC-Cys142ins | >10 μM | >10 μM |
| | 2A1-HC-Cys254ins | >10 μM | >10 μM |
| | 2A1-HC-Cys255ins | >10 μM | >10 μM |
| | 2A1-HC-Cys258ins | >10 μM | >10 μM |
| | 2A1-HC-Cys259ins | >10 μM | >10 μM |
| | 2A1-HC-Cys354ins | >10 μM | >10 μM |
| | 2A1-HC-Cys355ins | >10 μM | >10 μM |
| | 2A1-HC-Cys357ins | >10 μM | >10 μM |
| | 2A1-HC-Cys378ins | >10 μM | >10 μM |
| | 2A1-HC-Cys379ins | >10 μM | >10 μM |
| | 2A1-HC-Cys386ins | >10 μM | >10 μM |
| | 2A1-HC-Cys387ins | >10 μM | >10 μM |
| | 2A1-HC-Cys410ins | >10 μM | >10 μM |
| Fixed-Point Coupling (TDC) | 2A1-LC-Cys110ins-mc-vc-PAB-MMAE TDC | 88.45 nM | 225.11 nM |
| | 2A1-LC-Cys111ins-mc-vc-PAB-MMAE TDC | 120.22 nM | 337.14 nM |
| | 2A1-LC-Cys142ins-mc-vc-PAB-MMAE TDC | 118.26 nM | 321.48 nM |
| | 2A1-HC-Cys254ins-mc-vc-PAB-MMAE TDC | 146.62 nM | 335.52 nM |
| | 2A1-HC-Cys255ins-mc-vc-PAB-MMAE TDC | 107.33 nM | 275.71 nM |
| | 2A1-HC-Cys258ins-mc-vc-PAB-MMAE TDC | 121.47 nM | 301.32 nM |
| | 2A1-HC-Cys259ins-mc-vc-PAB-MMAE TDC | 114.24 nM | 358.14 nM |
| | 2A1-HC-Cys354ins-mc-vc-PAB-MMAE TDC | 118.39 nM | 370.21 nM |
| | 2A1-HC-Cys355ins-mc-vc-PAB-MMAE TDC | 114.95 nM | 292.15 nM |
| | 2A1-HC-Cys357ins-mc-vc-PAB-MMAE TDC | 104.85 nM | 119.2 nM |
| | 2A1-HC-Cys378ins-mc-vc-PAB-MMAE TDC | 67.57 nM | 223.3 nM |
| | 2A1-HC-Cys379ins-mc-vc-PAB-MMAE TDC | 98.47 nM | 189.15 nM |
| | 2A1-HC-Cys386ins-mc-vc-PAB-MMAE TDC | 94.12 nM | 202.48 nM |

APPENDED TABLE 5-continued

IC50 test results showing TDC cytotoxicity for EGFRwt-overexpressing cell line A431 and the EFGRvIII-overexpressing cell line U87-EGFRvIII

| Compound | MTS | |
|---|---|---|
| | A431 | U87MG-EGFRvIII |
| 2A1-HC-Cys387ins-mc-vc-PAB-MMAE TDC | 48.62 nM | 104.8 nM |
| 2A1-HC-Cys410ins-mc-vc-PAB-MMAE TDC | 56.69 nM | 117.9 nM |

The results shown in Table 5 shown that 2A1-LC-Cys110ins-mc-vc-PAB-MMAE TDC, 2A1-LC-Cys111ins-mc-vc-PAB-MMAE TDC, 2A1-LC-Cys142ins-mc-vc-PAB-MMAE TDC, 2A1-HC-Cys254ins-mc-vc-PAB-MMAE TDC, 2A1-HC-Cys255ins-mc-vc-PAB-MMAE TDC, 2A1-HC-Cys258ins-mc-vc-PAB-MMAE TDC, 2A1-HC-Cys259ins-mc-vc-PAB-MMAE TDC, 2A1-HC-Cys354ins-mc-vc-PAB-MMAE TDC, 2A1-HC-Cys355ins-mc-vc-PAB-MMAE TDC, 2A1-HC-Cys357ins-mc-Vc-PAB-MMAE TDC, 2A1-HC-Cys378ins-mc-vc-PAB-MMAE TDC, 2A1-HC-Cys379ins-mc-vc-PAB-MMAE TDC, 2A1-HC-Cys386ins-mc-VC-PAB-MMAE TDC, 2A1-HC-Cys387ins-mc-vc-PAB-MMAE TDC and 2A1-HC-Cys410ins-mc-vc-PAB-MMAE exhibit significant cytotoxic activity against EGFRwt-overexpressing cell line A431 and the EFGRvIII-overexpressing cell line U87-EGFRvIII.

The present invention is not limited to the scope of the embodiments disclosed in the examples; said examples are used to exemplify several aspects of the invention, and any embodiments that are functionally equivalent shall fall within the scope of the present invention. Indeed, in addition to the examples shown and described herein, additional variants of the invention should also be apparent to a person skilled in the art and fall within the scope of the claims appended hereto.

Example 20. Plasma Stability Testing

A fixed amount of TDC sample was added to human plasma for which human IgG had already been removed, with each TDC tube prepared in triplicate; next, incubation in a 37° C. water bath was performed for 0 hours, 24 hours and 72 hours, after which the TDC sample was removed and 100 ul of Protein A (MabSelect SuRe™ LX Lot: #10221479GE, washed with PBS) was added to each tube; adsorption was then allowed to proceed under agitation on a vertical mixer for two hours, followed by washing and elution to obtain incubated TDC. HIC-HPLC and RP-HPLC testing was performed on TDC samples incubated for a fixed amount of time to determine the plasma stability of the samples.

Figure 15:
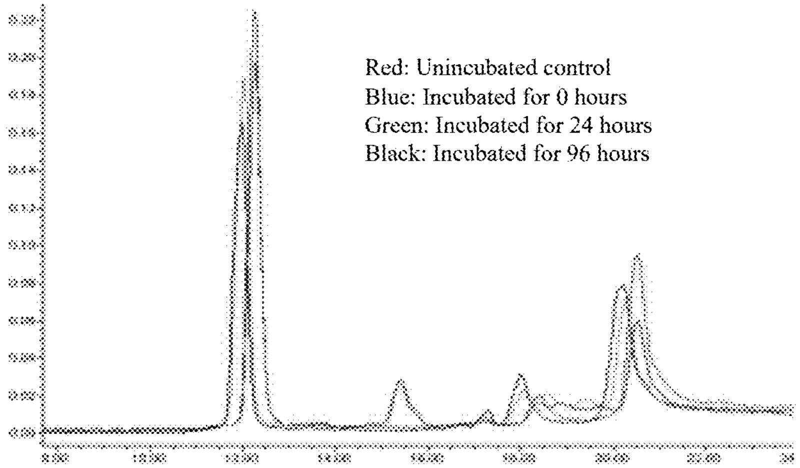
FIGS. 15-17 show HIC-HPLC plasma stability test results demonstrating that the three molecules of 2A1-HC-Cys357ins-mc-vc-PAB-MMAE TDC, 2A1-HC-Cys410ins-mc-vc-PAB-MMAE TDC, 2A1-HC-Cys387ins-mc-vc-PAB-MMAE TDC 2A1-HC-Cys378ins-mc-vc-PAB-MMAE TDC exhibit good plasma stability.
Figure 16:
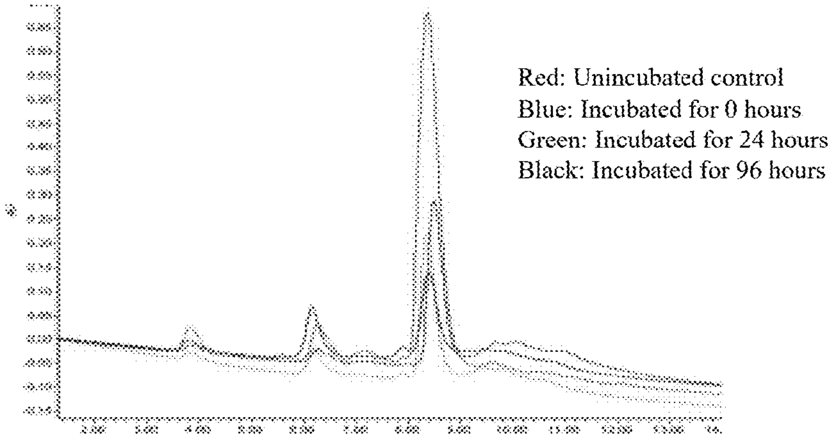
Figure 17:
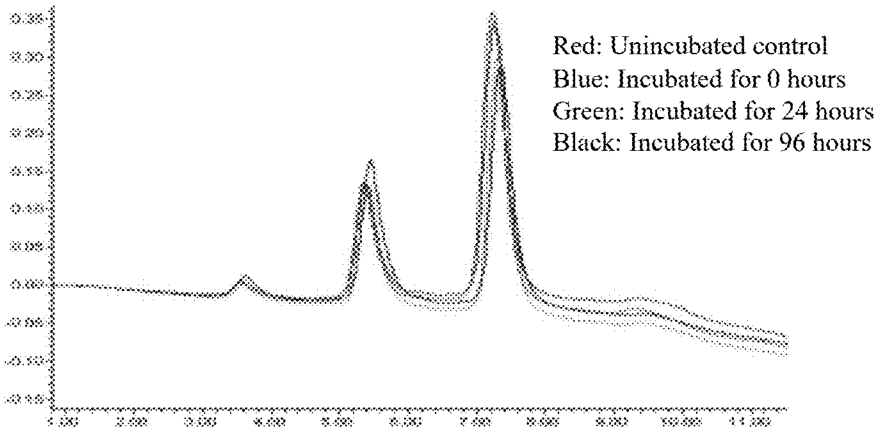

Appended FIGS. 15 through 17: 2A1-HC-Cys357ins-mc-vc-PAB-MMAE TDC, 2A1-HC-Cys410ins-mc-vc-PAB-MMAE TDC, 2A1-HC-Cys387ins-mc-vc-PAB-MMAE TDC 2A1-HC-Cys378ins-mc-vc-PAB-MMAE TDC HIC-HPLC plasma stability test results. The results shown in the figures demonstrate that the three molecules exhibit good plasma stability.

APPENDED TABLE 6

TDC plasma stability test results

| | Compound | TDC Plasma Incubation Time and Change in DAR | | |
|---|---|---|---|---|
| | | 0 h | 24 h | 96 h |
| Fixed-Point Coupling (TDC) | 2A1-LC-Cys110ins-mc-vc-PAB-MMAE TDC | 1.76 | 1.78 | 1.77 |
| | 2A1-LC-Cys111ins-mc-vc-PAB-MMAE TDC | 1.80 | 1.75 | 1.73 |
| | 2A1-LC-Cys142ins-mc-vc-PAB-MMAE TDC | 1.75 | 1.73 | 1.72 |
| | 2A1-HC-Cys254ins-mc-vc-PAB-MMAE TDC | 1.75 | 1.72 | 1.70 |
| | 2A1-HC-Cys255ins-mc-vc-PAB-MMAE TDC | 1.76 | 1.73 | 1.69 |
| | 2A1-HC-Cys258ins-mc-vc-PAB-MMAE TDC | 1.72 | 1.68 | 1.62 |
| | 2A1-HC-Cys259ins-mc-vc-PAB-MMAE TDC | 1.73 | 1.70 | 1.65 |
| | 2A1-HC-Cys354ins-mc-vc-PAB-MMAE TDC | 1.75 | 1.64 | 1.58 |
| | 2A1-HC-Cys355ins-mc-vc-PAB-MMAE TDC | 1.74 | 1.68 | 1.63 |
| | 2A1-HC-Cys357ins-mc-vc-PAB-MMAE TDC | 1.804 | 1.79 | 1.74 |
| | 2A1-HC-Cys378ins-mc-vc-PAB-MMAE TDC | 1.60 | 1.46 | 1.34 |
| | 2A1-HC-Cys379ins-mc-vc-PAB-MMAE TDC | 1.79 | 1.72 | 1.64 |
| | 2A1-HC-Cys386ins-mc-vc-PAB-MMAE TDC | 1.73 | 1.70 | 1.65 |
| | 2A1-HC-Cys387ins-mc-vc-PAB-MMAE TDC | 1.80 | 1.51 | 1.48 |
| | 2A1-HC-Cys410ins-mc-vc-PAB-MMAE TDC | 1.71 | N/A | 1.39 |

Example 21: Drug Efficacy Testing in Tumor-Bearing Mice

Figure 18:
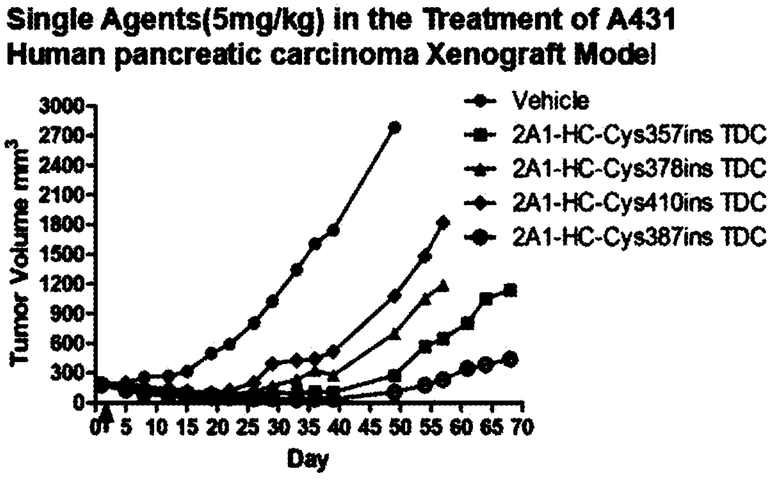
FIG. 18 shows 2A1-HC-Cys357ins-mc-vc-PAB-MMAE (2A1-HC-Cys357ins TDC), 2A1-HC-Cys410ins-mc-vc-PAB-MMAE (2A1-HC-Cys410ins TDC), 2A1-HC-Cys387ins-mc-vc-PAB-MMAE (2A1-HC-Cys387ins TDC) and 2A1-HC-Cys378ins-mc-vc-PAB-MMAE (2A1-HC-Cys378ins TDC) were administered via a single tail vein injection at a dose of 5 mg/kg, producing a significant anti-tumor effect.

As part of the present invention, we established a subcutaneous transplantation tumor model of the human pancreatic cancer cell line BxPC3 in nude mice to evaluate the in vivo efficacy of TDC conjugates such as 2A1-HC-Cys357ins-mc-vc-PAB-MMAE. $5\times10^6$ A431 cells were injected subcutaneously into the backs of 4 to 6-week-old BALB/c nude mice and when the average tumor size grew to approximately 150 to 200 $mm^3$, the mice were randomly grouped into groups of six mice each. On Day 1, 2A1-HC-Cys357ins-mc-vc-PAB-MMAE (2A1-HC-Cys357ins TDC), 2A1-HC-Cys410ins-mc-vc-PAB-MMAE (2A1-HC-Cys410ins TDC), 2A1-HC-Cys387ins-mc-vc-PAB-MMAE (2A1-HC-Cys387ins TDC) and 2A1-HC-Cys378ins-mc-vc-PAB-MMAE (2A1-HC-Cys378ins TDC) were administered via a single tail vein injection at a dose of 5 mg/kg (FIG. 6) and data were gathered in the form of mean tumor volume±SE at the time of measurement. Appended FIG. 18: 2A1-HC-Cys357ins-mc-vc-PAB-MMAE (2A1-HC-Cys357ins TDC), 2A1-HC-Cys410ins-mc-vc-PAB-MMAE (2A1-HC-Cys410ins TDC), 2A1-HC-Cys387ins-mc-vc-PAB-MMAE (2A1-HC-Cys387ins TDC) and 2A1-HC-Cys378ins-mc-vc-PAB-MMAE (2A1-HC-Cys378ins TDC) were administered via a single tail vein injection at a dose of 5 mg/kg, producing a significant anti-tumor effect.

The invention claimed is:

1. A cysteine-modified antibody-toxin conjugate, comprising an antibody and a cytotoxin, wherein the antibody comprises an inserted cysteine at one or more cysteine insertion sites at positions 110, 111, or 142 within the light chain constant region, or at positions 254, 255, 258, 259, 354, 355, 357, 378, 379, 386, 387 or 410 within the heavy chain constant region.

2. The cysteine-modified antibody-toxin conjugate of claim 1, wherein the amino acid sequence of said cysteine insertion site comprises one or more of:

LC-110ins: (SEQ ID NO: 45)
EIKRTCVAAPS;

-continued

LC-111ins: (SEQ ID NO: 46)
IKRTVCAAPSV;

LC-142ins: (SEQ ID NO: 47)
NNFYPCREAKV;

HC-254ins: (SEQ ID NO: 48)
ISRTPCEVTCV;

HC-255ins: (SEQ ID NO: 49)
SRTPECVTCVV;

-continued

HC-258ins:
(SEQ ID NO: 50)
PEVTCCVVVDV;

HC-259ins:
(SEQ ID NO: 51)
EVTCVCVVDVS;

HC-354ins:
(SEQ ID NO: 52)
PSRDECLTKNQ;

HC-355ins:
(SEQ ID NO: 53)
SRDELCTKNQV;

HC-357ins:
(SEQ ID NO: 54)
DELTKCNQVSL;

HC-378ins:
(SEQ ID NO: 55)
IAVEWCESNGQ;

HC-379ins:
(SEQ ID NO: 56)
AVEWECSNGQP;

HC-386ins:
(SEQ ID NO: 57)
GQPENCNYKTT;

-continued

HC-387ins:
(SEQ ID NO: 58)
QPENNCYKTTP;

HC-410ins:
(SEQ ID NO: 59)
KLTVDCKSRWQ.

3. The cysteine-modified antibody-toxin conjugate of claim 1, wherein the cytotoxin is conjugated to the sulfhydryl group of the inserted cysteine via a linker, wherein the antibody light chain have an amino acid sequence corresponding to: EIKRTCVAAPS (SEQ ID NO:45), IKRTVCAAPSV (SEQ ID NO:46), or NNFYPCREAKV (SEQ ID NO:47), wherein the antibody heavy chain have an amino acid sequence corresponding to: ISRTPCEVTCV (SEQ ID NO:48), SRTPECVTCVV (SEQ ID NO:49), PEVTCCVVVDV (SEQ ID NO: 50), EVTCVCVVDVS (SEQ ID NO:51), PSRDECLTKNQ (SEQ ID NO:52), SRDELCTKNQV (SEQ ID NO:53), DELTKCNQVSL (SEQ ID NO:54), IAVEWCESNGQ (SEQ ID NO:55), AVEWECSNGQP (SEQ ID NO:56), GQPENCNYKTT (SEQ ID NO:57), QPENNCYKTTP (SEQ ID NO:58), or KLTVDCKSRWQ (SEQ ID NO:59), and wherein C corresponds to the inserted cysteine in the light or heavy chain of the cysteine-modified antibody.

4. The cysteine-modified antibody-toxin conjugate of claim 3, wherein said cytotoxin is selected from a group consisting of MMAE, MMAF, PBD, SN-38, Dox, Amanitin having the following molecular formulas:

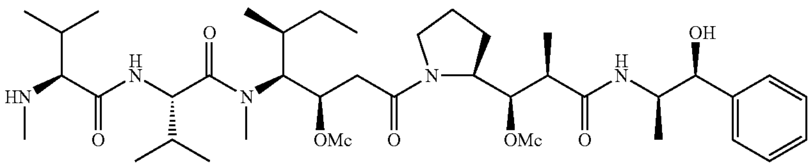

MMAE

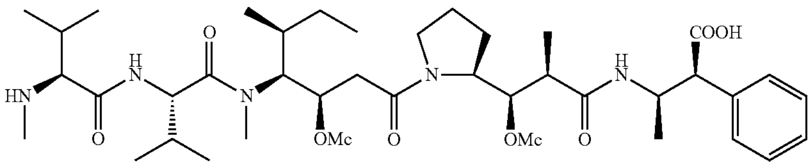

MMAF

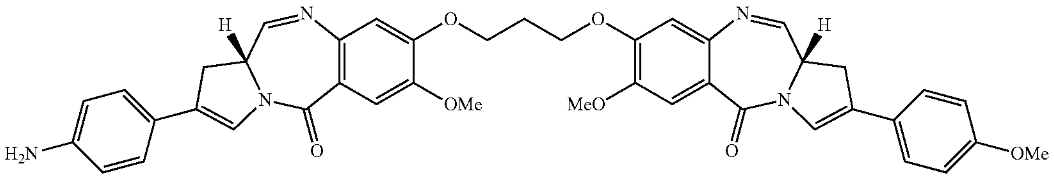

PBD

-continued

SN-38

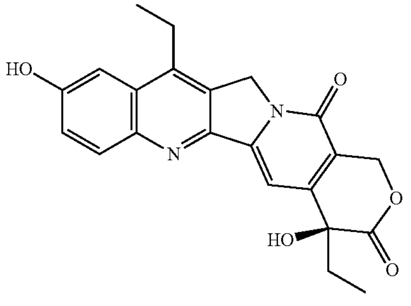

SN-38

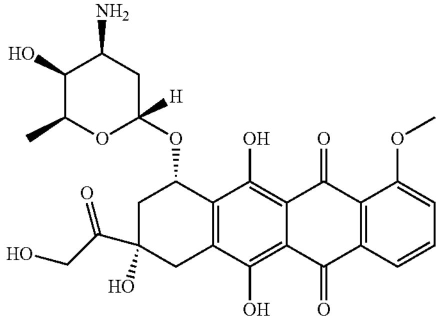

DOX

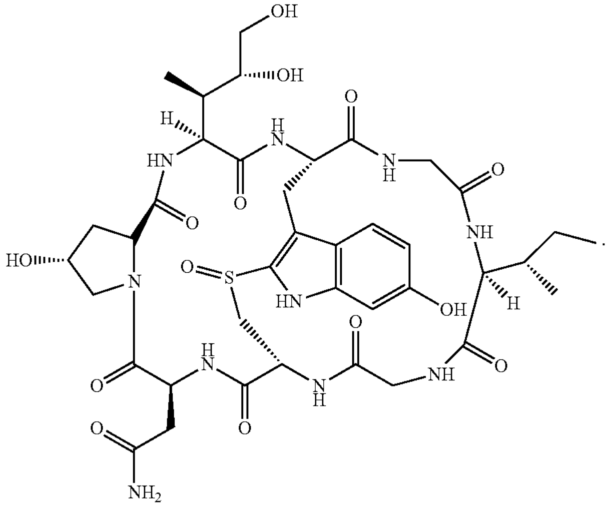

Amanitin

5. The cysteine-modified antibody-toxin conjugate of claim 1, wherein said antibody light chain comprises kappa isotype.

6. The cysteine-modified antibody-toxin conjugate of claim 1, wherein said antibody heavy chain comprises IgG1, IgG2, IgG3 or IgG4 isotypes.

7. The cysteine-modified antibody-toxin conjugate of claim 1, wherein said inserted cysteine comprises a sulfhydryl group before being coupled to the cytotoxin.

8. The cysteine-modified antibody-toxin conjugate of claim 1, wherein said antibody light chain comprises lambda isotype.

9. The cysteine-modified antibody-toxin conjugate of claim 1, wherein said cytotoxin to the antibody ratio ranges from 1.6 to 2.0 or from 3.2 to 4.0.

10. The cysteine-modified antibody-toxin conjugate of claim 1, prepared by, reducing a cysteine-modified antibody comprising a protected cysteine having a protected sulfhydryl group and a protecting group, using a reducing agent to remove the protecting group from the protected cysteine to provide a removed protecting group and a reduced antibody comprising a de-protected cysteine having a sulfhydryl group, removing the removed protecting group and any excess reducing agent using a method comprising cation exchange chromatography or ultrafiltration, oxidizing the reduced antibody using an oxidizing agent to reattach the interchain disulfide bonds of the antibody, coupling the cytotoxin with the sulfhydryl group on the inserted cysteine to provide the cysteine-modified antibody-toxin conjugate, and removing any uncoupled cytotoxin using a method comprising cation exchange chromatography or ultrafiltration.

* * * * *